(12) United States Patent
Yoshida

(10) Patent No.: US 11,576,638 B2
(45) Date of Patent: Feb. 14, 2023

(54) X-RAY IMAGING APPARATUS AND X-RAY IMAGE PROCESSING METHOD

(71) Applicant: Shimadzu Corporation, Kyoto (JP)

(72) Inventor: Takanori Yoshida, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 3 days.

(21) Appl. No.: 16/541,432

(22) Filed: Aug. 15, 2019

(65) Prior Publication Data

US 2020/0069276 A1 Mar. 5, 2020

(30) Foreign Application Priority Data

Sep. 5, 2018 (JP) .............................. JP2018-166137

(51) Int. Cl.
*G06T 7/00* (2017.01)
*A61B 6/00* (2006.01)
*G06T 5/50* (2006.01)

(52) U.S. Cl.
CPC .............. *A61B 6/504* (2013.01); *A61B 6/481* (2013.01); *G06T 5/50* (2013.01); *A61B 6/463* (2013.01); *A61B 6/5235* (2013.01); *A61B 6/582* (2013.01); *G06T 7/0012* (2013.01); *G06T 2207/10116* (2013.01); *G06T 2207/30104* (2013.01)

(58) Field of Classification Search
CPC ......... A61B 6/504; A61B 6/481; A61B 6/463; A61B 6/582; A61B 6/5235; A61B 6/5264; A61B 6/54; G06T 5/50; G06T 2207/30104; G06T 7/0012; G06T 2207/10116; G06T 7/246; G06T 3/4069; G02B 27/023

See application file for complete search history.

(56) References Cited

U.S. PATENT DOCUMENTS

| | | | |
|---|---|---|---|
| 7,609,814 B2 | 10/2009 | Baumgart | |
| 7,715,528 B2 | 5/2010 | Miura | |
| 9,536,302 B2 | 1/2017 | Nakano | |
| 9,659,366 B2 | 5/2017 | Yokota et al. | |
| 2012/0177277 A1 | 7/2012 | Florent et al. | |
| 2017/0192075 A1* | 7/2017 | Nakai | G01R 33/4828 |
| 2018/0232861 A1* | 8/2018 | Hamauzu | G06T 5/002 |

(Continued)

FOREIGN PATENT DOCUMENTS

| | | |
|---|---|---|
| JP | 2009-106502 A | 5/2009 |
| JP | 5029607 B2 | 7/2012 |

(Continued)

OTHER PUBLICATIONS

Liang, Zifei, et al. "Combining coarse and fine registration for video frame super-resolution reconstruction." Journal of Electronic Imaging 23.6 (2014): 063018. (Year: 2014).*

(Continued)

*Primary Examiner* — Claire X Wang
*Assistant Examiner* — Han Hoang
(74) *Attorney, Agent, or Firm* — Muir Patent Law, PLLC

(57) ABSTRACT

An image synthesis unit of an X-ray imaging apparatus is configured to correct a synthesis target image or a transparent image based on movement information of a feature point and movement information of a pixel and generate a synthesized image by synthesizing a corrected synthesis target image and a transparent image or synthesizing a synthesis target image and a corrected transparent image.

15 Claims, 10 Drawing Sheets

(56) References Cited

U.S. PATENT DOCUMENTS

2018/0279986 A1* 10/2018 Nagae .................. A61B 6/06
2019/0213741 A1*  7/2019 Nagae .................. G06T 7/33
2019/0388051 A1* 12/2019 Morita ............... A61B 6/5264

FOREIGN PATENT DOCUMENTS

| JP | 2013-039274 A | 2/2013 |
|----|---------------|--------|
| JP | 2013505766 A | 2/2013 |
| JP | 5366618 B2 | 9/2013 |
| JP | 2013-212364 A | 10/2013 |
| JP | 2015009126 A | 1/2015 |
| JP | 2016-041166 A | 3/2016 |
| JP | 2018129738 A | 8/2018 |
| WO | 2019/053935 A1 | 3/2019 |

OTHER PUBLICATIONS

[Item U Continued] https://www.spiedigitallibrary.org/journals/journal-of-electronic-imaging/volume-23/issue-6/063018/Combining-coarse-and-fine-registration-for-video-frame-super-resolution/10.1117/1.JEI.23.6.063018.full?SSO=1.*

Notice of Reasons for Refusal dated Apr. 26, 2022 for corresponding Japanese Patent Application No. JP 2018-166137, submitted with a machine translation.

Notice of Reasons for Refusal dated Jan. 5, 2022, in relation to corresponding Japanese Patent Application No. 2018-166137.

* cited by examiner

X-RAY IMAGING APPARATUS AND X-RAY IMAGE PROCESSING METHOD

CROSS-REFERENCE TO RELATED APPLICATIONS

The related application number JP2018-166137, an X-ray imaging apparatus and an X-ray image processing method, filed on Sep. 5, 2018, and invented by Takanori Yoshida, upon which this patent application is based are hereby incorporated by reference.

BACKGROUND OF THE INVENTION

Field of the Invention

The present invention relates to an X-ray imaging apparatus and an X-ray image processing method.

Description of the Background Art

Conventionally, an X-ray imaging apparatus and an X-ray image processing method are known in which a synthesis target image and a transparent image are synthesized to generate a synthesized image. Such an X-ray imaging apparatus is disclosed in, for example, Japanese Patent No. 5366618.

Japanese Patent No. 5366618 discloses an X-ray image diagnostic apparatus in which road map data (synthesis target image) and transparent image data (transparent image) are displayed in a superimposed manner. In this X-ray image diagnostic apparatus, in order to suppress the positional displacement between the position of the imaging system that imaged the transparent image data and the position of the imaging system that imaged the road map data to be superimposed on the transparent image data, road map data imaged at the position of the imaging system closest to the position of the imaging system that imaged the transparent image data is extracted from a plurality of reference image data.

In detail, this X-ray image diagnostic apparatus is provided with a position detection means, a movement determination means, a road map data search means, and a display means. The position detection means is configured to detect the position information of the imaging system. The movement determination means is configured to determine the movement stop state showing the state in which the movement of the imaging system is stopped based on the position information detected by the position detection means at the time of collecting the transparent image data. The road map data search means is configured to extract, as road map data, the reference image data having the position information closest to the position information of the imaging system at the time when it is determined to be the movement stop state from a plurality of reference image data. Moreover, the display means is configured to display the road map data and the transparent image data in a superimposed manner (display the synthesized image).

However, in the X-ray image diagnostic apparatus as described in the above-described U.S. Pat. No. 5,366,618, in some cases, a subject moves (the body moves) relative to the imaging system while capturing a plurality of X-ray images. For this reason, in the X-ray image diagnostic apparatus described in the above-described U.S. Pat. No. 5,366,618, it is considered that there is a case in which the positional displacement may occur (the positional displacement between the subject and the imaging system may occur) due to the movement of the subject between the position of the subject reflected in the transparent image with respect to the imaging system at the time when it is determined to be a movement stop state and the position of the subject reflected in the road map data with respect to the imaging system at the time when the road map data is captured.

In this case, even in cases where road map data closest to the position of the imaging system of the transparent image data is extracted as an image constituting the synthesized image, it is considered that the X-ray images of the subject shifted from each other due to the movement of the subject are displayed in a superimposed manner. In this case, it is necessary to recapture the road map data (X-ray image), which increases the radiation exposure of the X-ray to the subject. In addition, when using a contrast agent, the usage of the contrast agent is increased. Therefore, in the conventional X-ray image diagnostic apparatus as described in the above-described U.S. Pat. No. 5,366,618, in the case of generating a synthesized image by synthesizing a synthesis target image and a transparent image captured at different time points, there is a problem that a synthesized image cannot be generated properly, which in turn may increase the radiation exposure of the X-ray to the subject.

SUMMARY OF THE INVENTION

The present invention has been made to solve the aforementioned problems, and one object objective of the present invention is to provide an X-ray imaging apparatus and an X-ray image processing method capable of suppressing an increase in radiation exposure of an X-ray to a subject by appropriately generating a synthesized image even when the subject moves after capturing a synthesis target image when generating an synthesized image by synthesizing the synthesis target image and a transparent image captured at different time points.

In order to attain the aforementioned objective, an X-ray imaging apparatus according to a first aspect of the present invention includes: an imaging unit including an X-ray generation unit configured to emit X-rays to a subject and an X-ray detection unit configured to detect X-rays from the X-ray generation unit transmitted through the subject, the imaging unit being configured to capture an X-ray image of the subject; a transparent image acquisition unit configured to acquire a transparent image which is the X-ray image captured by the imaging unit to radiographically inspect the subject and includes a feature point image; an image synthesis unit configured to synthesize the transparent image and a synthesis target image which is the X-ray image captured before a time when the transparent image is captured and is to be synthesized with the transparent image to generate a synthesized image; a reference image acquisition unit configured to acquire the X-ray image including the feature point image and captured before a time when the transparent image is captured as a reference image; and a movement information acquisition unit configured to extract the feature point image from each of the reference image and the transparent image, acquire movement information of a feature point based on the extracted feature point image, and acquire movement information of at least some of pixels belonging to the reference image based on the reference image and the transparent image, wherein the image synthesis unit is configured to correct the synthesis target image or the transparent image based on the movement information of the feature point and the movement information of the pixel and synthesize the corrected synthesis target image and the transparent image or synthesize the synthesis target image and the corrected transparent image to generate the synthesized image.

In the X-ray imaging apparatus according to one aspect of the present invention, as described above, the movement information acquisition unit is configured to acquire the movement information of the feature point and acquire the movement information of the pixel based on the feature point image of the reference image which is an X-ray image captured before the time when the transparent image is captured and the feature point image of the transparent image. Then, the image synthesis unit is configured to correct the synthesis target image or the transparent image based on the movement information of the feature point and the movement information of the pixel and generate the synthesized image by synthesizing the corrected synthesis target image and the transparent image or synthesizing the synthesis target image and the corrected transparent image.

Thus, even when the subject has moved with respect to the imaging unit after the synthesis target image and the reference image are captured, the synthesis target image or the transparent image can be corrected so as to correspond to the movement of the subject. For this reason, it is possible to suppress the synthesis of X-ray images (synthesis target image and transparent image) in which the positions of the feature points of the subject are mutually shifted. As a result, even in cases where the subject moves after capturing the synthesis target image when synthesizing the synthesis target image and the transparent image (X-ray image) captured at different time points to generate a synthesized image, a synthesized image can be generated appropriately (the positional displacement between images is suppressed). This eliminates the necessity of recapturing a synthesis target image, which makes it possible to suppress an increase in the radiation exposure of X-rays with respect to the subject P.

Note that it is not easy to follow the relatively fine movement of a subject only by the correction for the relatively large movement of the subject (the movement of the feature point itself) and it is not easy to cope with the large movement of the feature point itself of the subject only by the correction of the relatively small movement of the subject (movement in pixel unit).

On the other hand, in the present invention, as described above, the movement information acquisition unit is configured to acquire the movement information of the feature point and the movement information of the pixel as information for correcting the synthesis target image. With this, the movement information of the feature point is obtained as relatively broad range (macro) movement information in the reference image and the transparent image, and therefore it is possible to perform corrections with respect to a movement of the subject (relatively large movement). And, the movement information of the pixel is obtained as a movement of a relatively narrow range (micro) in the reference image and the transparent image, and therefore it is possible to perform a correction with respect to the movement of the subject of a relatively narrow range (relatively small movement). As a result, it is possible to correct the synthesis target image more appropriately by performing both of the correction for the relatively large movement of the subject and the correction for the relatively small movement of the subject, which mutually complement advantages and disadvantages. Therefore, even in the case of generating a synthesize image by synthesizing the synthesis target image and the X-ray image captured at different time points with each other, it is possible to more appropriately generate a synthesized image (in which the positional displacement between images is further suppressed).

In the X-ray imaging apparatus according to the first aspect of the present invention, preferably, the transparent image acquisition unit is configured to acquire the transparent image as a live image sequentially generated in real time, and the image synthesis unit is configured to correct the synthesis target image or the live image based on the movement information of the feature point and the movement information of the pixel and synthesize the corrected synthesis target image and the live image or synthesize the synthesis target image and the corrected live image to generate the synthesized image.

With this configuration, it is possible to correct the synthesis target image or the live image in response to the live image changes. Therefore, even in the case of synthesizing the live image that is displayed in real time and changes sequentially and the synthesis target image, a synthesized image can be generated appropriately. In this specification, "real time" means not only "immediately" or "simultaneously" but also the period during which an operator (manipulator) uses the X-ray imaging apparatus (state in which the operated or captured X-ray image is visible). Also, "a live image sequentially generated" is described to mean that, for example, an X-ray which is displayed while being updated for each frame of a plurality of X-ray images (for example, moving images) sequentially acquired.

In this case, it is preferable that the image synthesis unit is configured to correct the synthesis target image or the live image based on the movement information of the feature point and the movement information of the pixel each time the live image is acquired by the transparent image acquisition unit, and synthesize the corrected synthesis target image and the live image or synthesize the synthesis target image and the corrected live image to generate the synthesized image.

By configuring as described above, it is possible to correct the synthesis target image or the live image so as to be updated sequentially in correspondence with the live image to be updated. For this reason, even in the case of synthesizing the live image (for example) which changes sequentially and the synthesis target image, it is possible to generate a synthesized image (in which the positional displacement between images is suppressed) more appropriately. As a result, even in cases where an operator performs a medical treatment of a subject while visually recognizing the synthesized image which is to be displayed as a moving image, it is possible to generate a synthesized image in which positional displacements are suppressed more effectively.

In the X-ray imaging apparatus configured to generate a synthesized image by synthesizing the synthesis target image and the live image, preferably, the image synthesis unit is configured to acquire a difference image between a contrast image which is the X-ray image in a state in which a contrast agent is administered to a blood vessel of a lower limb of the subject and a non-contrast image which is the X-ray image in a state in which no contrast agent is administered to the blood vessel of the subject as the synthesis target image, correct the difference image or the live image based on the movement information of the feature point and the movement information of the pixel, and synthesize the corrected difference image and the live image or synthesize the difference image and the corrected live image to generate the synthesized image.

Here, in the X-ray imaging apparatus configured to generate a synthesized image by synthesizing a synthesis target image and a live image, the operator can perform various medical treatments by inserting a catheter into the blood vessel of the lower limb of the subject while viewing the synthesized image. In this case, a difference image (a difference image between a contrast image and a non-contrast image) constituted only by an image showing a blood vessel is used as a synthesis target image. Taking this point into consideration, in the present invention, the image synthesis unit is configured to generate a synthesized image by correcting a difference image or a live image and synthesizing the corrected difference image and the live image or synthesizing the difference image and the corrected live image. With this, when the operator performs various medical treatments by inserting a catheter into the lower limb blood vessel of the subject P, it is possible to provide an X-ray imaging apparatus capable of generating a synthesized image in which the positional displacement between images is effectively suppressed.

In this case, it is preferable that the image synthesis unit is configured to synthesize an inverted image in which at least a part of the corrected difference image is black and white inversion processed and the live image or synthesize an inverted image in which at least a part of the difference image is black and white inversion processed and the corrected live image to generate the synthesized image.

Here, for example, in cases where the image of the contrasted blood vessel in the synthesis target image is black and the image of the therapeutic device in the live image is black identical to the image of the blood vessel, in the synthesized image, it is considered that there are some cases in which it is difficult to distinguish between the image of the blood vessel imaged and the image of the therapeutic device.

On the other hand, in the present invention, by configuring as described above, in the difference image, a substantially black image (for example, a blood vessel image) is synthesized with the live image in a state of being converted to a substantially white image (for example, an image of substantially background color), and therefore the therapeutic device (for example, a catheter, a stent, a guide wire, etc.) in the portion corresponding to the blood vessel in the live image can be displayed in black (a color different from the image of the blood vessel). As a result, it is possible to make the operator visually recognize the appropriately enhanced image of the blood vessel while improving the visibility of the therapeutic device in the live image.

It should be noted that in this specification, "black" means, for example, having a relatively low luminance value in an image (pixel), and "white" means, for example, having a relatively high luminance value in an image (pixel).

In an X-ray imaging apparatus configured to generate a synthesized image by synthesizing the above-described inverted image and live image, preferably, the image synthesis unit is configured to synthesize the inverted image and the live image including an image in which at least one of a catheter, a stent, and a guide wire inserted in the subject is projected to generate the synthesized image.

By configuring as described above, it is possible to make the operator recognize the contrasted image of the blood vessel that is projected as a substantially background color by the inverted image and the image projecting at least one of a catheter, a stent, and a guide wire inserted in the subject in a manner as to be more easily distinguished.

In the X-ray imaging apparatus configured to generate a synthesized image by synthesizing the difference image and the live image described above, preferably, the reference image acquisition unit is configured to acquire the live image captured before the transparent image at an imaging position substantially the same as an imaging position of the synthesis target image as the reference image.

Here, in some cases, the synthesis target image (contrast image and non-contrast image) and the live image (for example, transparent image) have a different X-ray dose when they are captured. In this case, when a synthesis target image (difference image) is used as a reference image and a live image is used as a transparent image, the luminance is different due to the difference in the X-ray dose irradiated even with the same feature point image. Therefore, it is considered that when the feature point image of the reference image and the feature point image of the transparent image are associated (matched), it is necessary to perform a luminance correction.

On the other hand, in the present invention, by configuring the reference image acquisition unit so as to obtain a live image captured before the transparent image as the reference image, a feature point image of a reference image (live image) and a feature point image of a transparent image (live image) can be associated with each other by live images having X-ray irradiation doses substantially equal to each other. This makes it possible to correct the synthesis target image while suppressing the complication of the control processing at the time of association since the control processing for correcting the luminance is unnecessary.

In the X-ray imaging apparatus configured to generate a synthesized image by synthesizing the difference image and the live image described above, preferably, the reference image acquisition unit is configured to acquire the contrast image as the reference image.

By configuring as described above, the contrast image which is an image including the image of the contrasted blood vessel remaining in the difference image (synthesis target image) and the image of the blood vessel of the synthesis target image are captured at the same time, the synthesis target image can be corrected more accurately than when a live image captured at a point later than the contrast image is acquired as a reference image.

In the X-ray imaging apparatus configured to generate a synthesized image by synthesizing the difference image and the live image described above, preferably, the reference image acquisition unit is configured to acquire the non-contrast image as the reference image.

Here, since the image of the contrasted blood vessel in the contrast image is a relatively characteristic image, when the contrast image is used as a reference image, there is a possibility that the image of the blood vessel is extracted as a feature point. On the other hand, in the live image (transparent image), the blood vessel is not imaged and it is unlikely that the blood vessel is extracted as a feature point. In this case, it is considered that different feature points may be extracted between the reference image and the transparent image.

On the other hand, in the present invention, by configuring the reference image acquisition unit so as to acquire the non-contrast image as the reference image, the non-contrast image that does not contain the image of the constructed blood vessel is configured as a reference image. Therefore, it is possible to suppress extraction of feature points different from each other in the reference image and the transparent image. As a result, since the feature points can be easily associated with each other, the movement information of the feature point can be easily obtained. In addition, it is possible to increase the irradiation dose of X-rays in the non-contrast image as compared with acquiring a live image as a reference image. Therefore, the reference image can be configured as a relatively sharp image.

In the X-ray imaging apparatus according to the first aspect of the present invention, preferably, the movement information acquisition unit is configured to correct the reference image based on the movement information of the feature point when a movement amount from the feature point image of the reference image to the feature point image of the transparent image exceeds a movement amount threshold value, and acquire movement information of the pixel based on the corrected reference image and the transparent image.

By configuring as described above, when the position of the feature point has moved relatively largely with respect to the imaging unit by the relatively large moving of the subject P (when the shift amount exceeds the threshold value), the reference image can be corrected based on the movement information of the feature point. For example, when the movement of the subject is relatively small (when the movement amount does not exceed a movement amount threshold value), by correcting the synthesis target image (by correcting only the relatively small movement of the subject) based on the movement information of the pixel without performing the control processing to correct the reference image, the synthesized image can be generated appropriately while reducing the control burden of the image synthesis unit.

In the X-ray imaging apparatus according to the first aspect of the present invention, preferably, the movement information acquisition unit is configured to extract a plurality of the feature point images from the reference image, extract a plurality of the feature point images from the transparent image, correct the reference image so as to move by a mean value of the movement amount from the feature point image of the reference image to the feature point image of the transparent image, and acquire the movement information of the pixel based on the corrected reference image and the transparent image.

By configuring as described above, since the reference image is corrected based on the mean value of a plurality of movement amounts, compared with the case in which a movement amount of only one feature point is used, it is possible to obtain more accurately the information of the movement of the entire subject reflected in the reference image and the transparent image.

In the X-ray imaging apparatus according to the first aspect of the present invention, preferably, the movement information acquisition unit is configured to acquire a movement map representing a movement direction and a movement amount of at least some of pixels belonging to the reference image based on the reference image and the transparent image, and acquire a smoothing movement map in which high frequency components of the movement map in a spatial direction is suppressed as the movement information of the pixel.

By configuring as described above, even in cases where an error occurs in the movement map due to the generation of the movement map for each pixel by acquiring a smoothing movement map in which high frequency components of the movement map in the spatial direction are suppressed as the movement information of the pixel, the influence of the error can be reduced by suppressing the high frequency components in the spatial direction. As a result, a synthesis target image and a transparent image can be properly synthesized considering not only the linear behavior of the subject between two X-ray images captured at different time points but also the non-linear behavior (relatively complex behavior).

The X-ray phase imaging apparatus according to a second aspect of the present invention, an X-ray image processing method includes: acquiring a transparent image which is an X-ray image for radiographically inspecting a subject and includes a feature point image; acquiring a reference image which is an X-ray image captured before a time when the transparent image is captured and includes the feature point image; extracting the feature point image from each of the reference image and the transparent image; acquiring movement information of a feature point based on the extracted feature point image; acquiring movement information of at least some of pixels belonging to the reference image based on the reference image and the transparent image; correcting a synthesis target image which is the X-ray image of the subject or the transparent image based on the movement information of the feature point and movement information of the pixel; and generating a synthesized image by synthesizing the corrected synthesis target image and the transparent image or synthesizing the synthesis target image and the corrected transparent image.

In the X-ray image processing method according to the second aspect of the present invention, with such a configuration, it is possible to provide an X-ray image processing method capable of suppressing an increase in radiation exposure of an X-ray to a subject by appropriately generating a synthesized image even when the subject has moved after capturing a synthesis target image when generating an synthesized image by synthesizing a synthesis target image and a transparent image captured at different time points.

DESCRIPTION OF PREFERRED EMBODIMENTS

Hereinafter, embodiments embodying the present invention will be described based on the attached drawings.

First Embodiment

The configuration of the X-ray imaging apparatus 100 according to the first embodiment of the present invention will be described with reference to FIG. 1 to FIG. 8.
(Configuration of X-Ray Imaging Apparatus)

Figure 1:
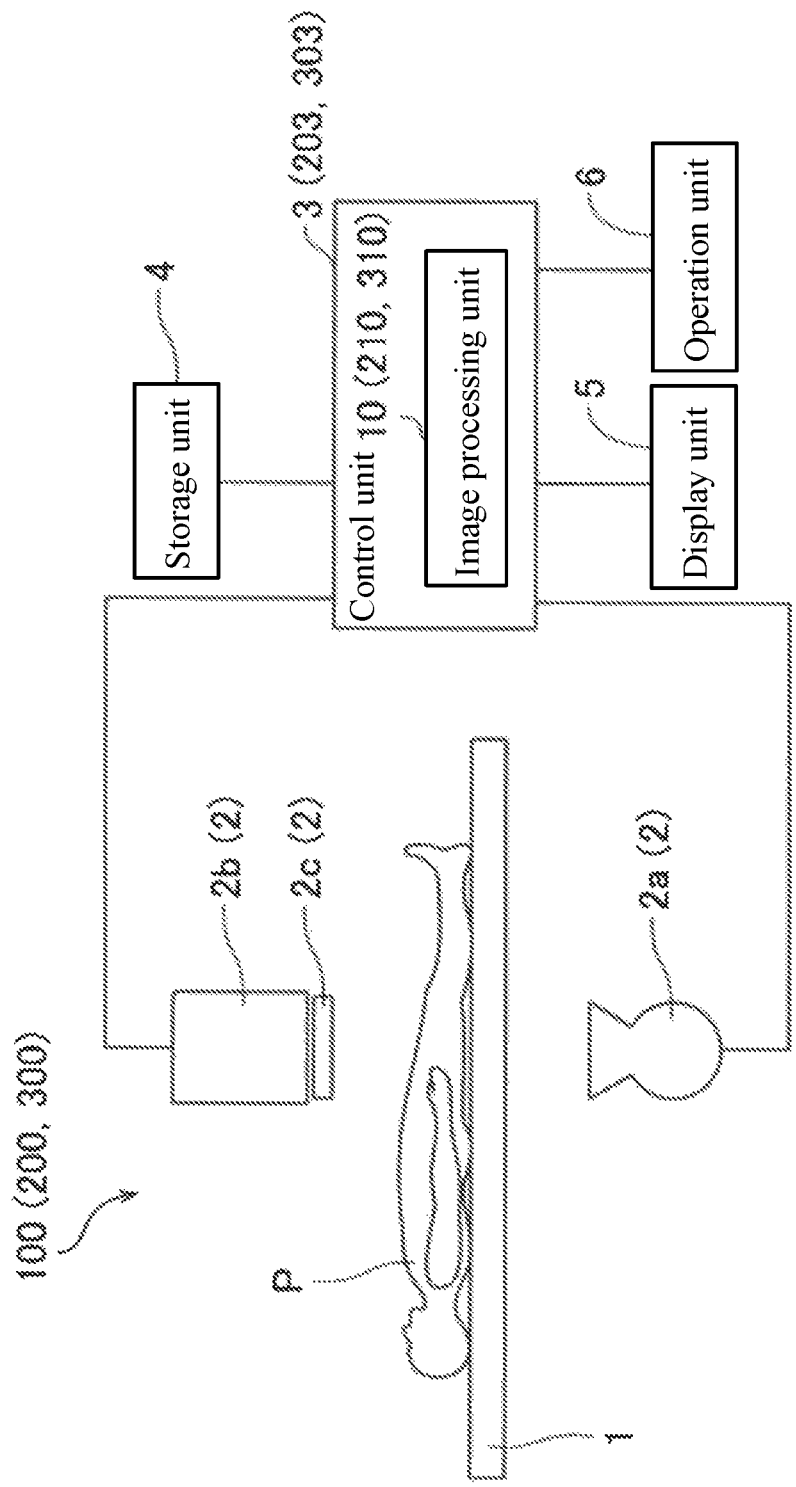
FIG. 1 is a view showing an overall configuration of an X-ray imaging apparatus according to first to third embodiments.

As shown in FIG. 1, the X-ray imaging apparatus 100 (radiographic imaging apparatus) according to the first embodiment is provided with a top board 1 on which a subject P is laid, an imaging unit 2 for capturing an X-ray image R of the subject P, and a control unit 3 for controlling various configurations of the X-ray imaging apparatus 100, a storage unit 4 for storing captured X-ray images R, etc., a display unit 5 for displaying the X-ray image R, etc., and an operation unit 6 for receiving input operations from an operator.

It should be noted that in the following description, the "operator" is not limited to those who perform medical treatments of the subject P, but also is described as a "manipulator" who simply manipulates the X-ray imaging apparatus 100 without directly participating in the medical treatment of the subject P.

Figure 2:
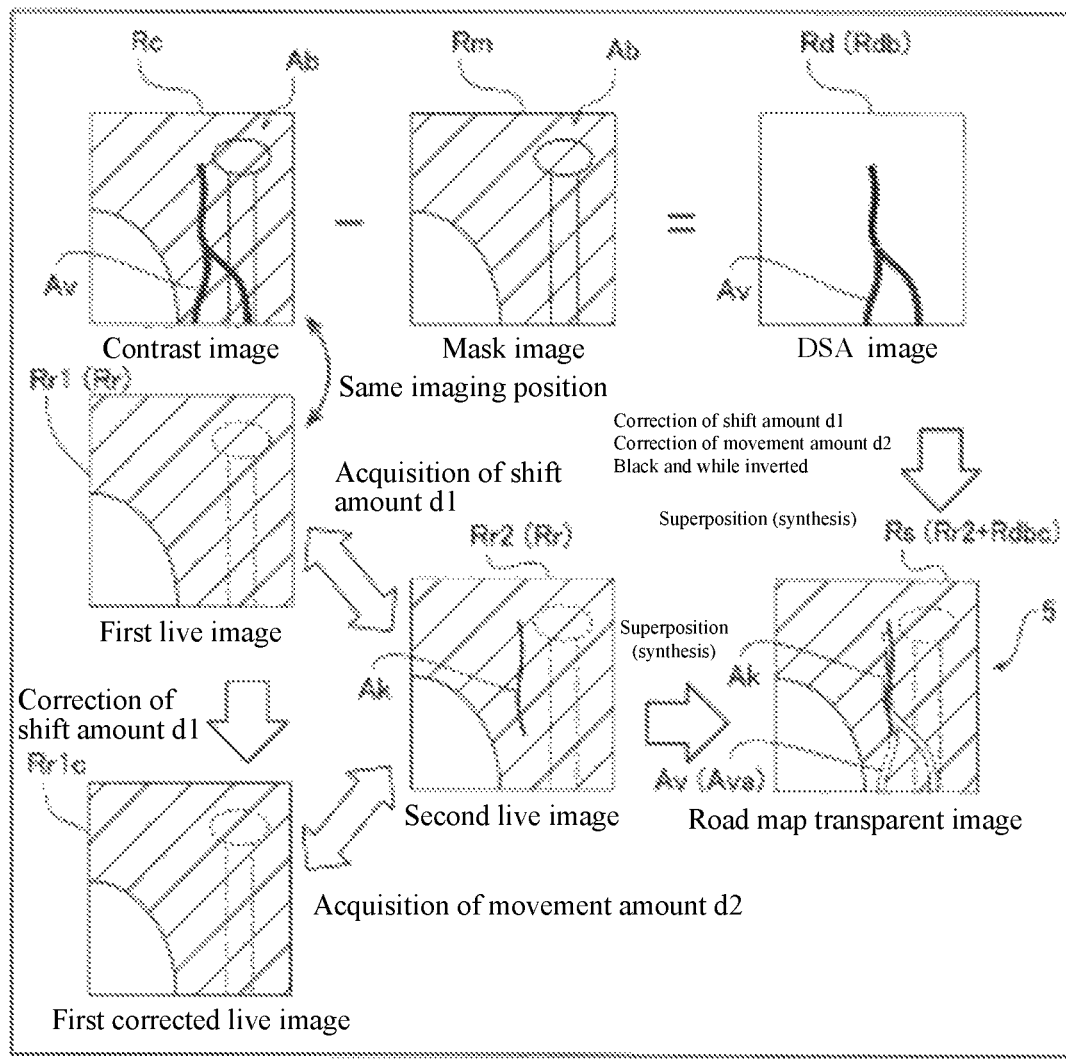
FIG. 2 is a diagram for explaining acquisition of a shift amount of the X-ray imaging apparatus, acquisition of a movement amount, and generation of a road map transparent image according to the first embodiment.

As shown in FIG. 2, the X-ray imaging apparatus 100 is configured to continuously capture an X-ray image R of the subject P to acquire a live image Rr (moving image) which is sequentially generated in real time. Further, the X-ray imaging apparatus 100 is configured to capture the live image Rr as a transparent image that radiographically inspects the subject P by reducing the irradiation dose of X-rays than in a contrast image Rc and a mask image Rm. With this, it becomes possible for the operator using the X-ray imaging apparatus 100 to perform various medical treatments by inserting a therapeutic device, such as, e.g., a catheter, into the blood vessel of the subject P (for example, the blood vessel of the lower limb of the subject P) while visually recognizing the live image Rr (transparent image) of the subject P.

Further, the X-ray imaging apparatus 100 is configured to display a road map transparent image Rs obtained by synthesizing a DSA image Rd which is a difference image between a contrast image Rc and a mask image Rm and a live image Rr by the display unit 5. Here, the X-ray imaging apparatus 100 according to the first embodiment is configured to perform, when generating the road map transparent image Rs, both of the correction (macro position adjustment correction) processing of extracting the feature point image F (see FIG. 4) and correcting the feature point based on the extracted feature point image F based on the movement information (shift amount d1 which will be described later) and the correction (micro position adjustment correction) processing which is correction processing performed based on the movement information (movement amount d2 which will be described later) of the pixel and uses the Flex-APS (Flexible Active Pixel Shift) technique.

(Configuration of Each Part of X-Ray Imaging Apparatus)

As shown in FIG. 1, the top board 1 is configured as an examination table on which the subject P is laid. The top board 1 is provided with a drive unit, and is configured to be movable by the command of the control unit 3 based on the input operation of the operation unit 6.

The imaging unit 2 is provided with an X-ray generation unit 2a for irradiating the subject P with X-rays, and an X-ray detection unit 2b for detecting the X-rays from the X-ray generation unit transmitted through the subject P. The X-ray generation unit 2a is configured as an X-ray tube device arranged on one side of the top board 1. The X-ray generation unit 2a includes an X-ray source, and is configured to be able to emit X-rays when a voltage is applied by an X-ray tube drive unit (not shown). The X-ray detection unit 2b is configured as an FPD (flat panel detector) arranged on the other side of the top board 1, and is configured so that X-rays can be detected. In the vicinity of the X-ray generation unit 2a, a collimator 2c is provided to adjust the irradiation field of the X-rays emitted from the X-ray generation unit 2a.

The control unit 3 is a computer configured so as to include a CPU (Central Processing Unit), a ROM (Read Only Memory), a RAM (Random Access Memory), and the like. The control unit 3 includes an image processing unit 10 that synthesizes X-ray images R obtained by X-ray imaging the internal structure of the subject P based on the detection signal sent from the X-ray detection unit 2b to generate a road map transparent image Rs.

The control unit 3 is configured to perform the control of switching between the road map transparent image capturing mode and the DSA image capturing mode based on the input operation of the operation unit 6 by the operator. In the road map transparent image capturing mode, the control unit 3 controls imaging of the live image Rr, while in the DSA image capturing mode, the control unit 3 controls imaging of a contrast image Rc and a mask image Rm.

The storage unit 4 includes, for example, a nonvolatile memory. The storage unit 4 stores a program used for processing the control unit 3, and is configured to store each X-ray image R (a mask image Rm, a contrast image Rc, a DSA image Rd, a live image Rr, and a road map transparent) generated by the image processing unit 10 image Rs), and the like.

The display unit 5 is configured as, for example, a liquid crystal display. The display unit 5 is configured so that a road map transparent image Rs (see FIG. 2), which will be described later, generated by the image processing unit 10 can be displayed. For example, display unit 5 is configured to display a road map transparent image Rs as a moving image.

The operation unit 6 is configured by, for example, an input button switch, a keyboard, a touch panel, or a mouse.
(Configuration of Image Processing Unit)

The image processing unit 10 is a computer configured so as to include a processor, such as, e.g., a GPU (Graphics Processing Unit) and an FPGA (Field-Programmable Gate Array) configured for image processing. The image processing unit 10 functions as an image processing apparatus by executing the image processing program stored in the storage unit 4. The X-ray image processing method, which will be described later, is a control processing method to be executed in the image processing unit 10.

Figure 3:
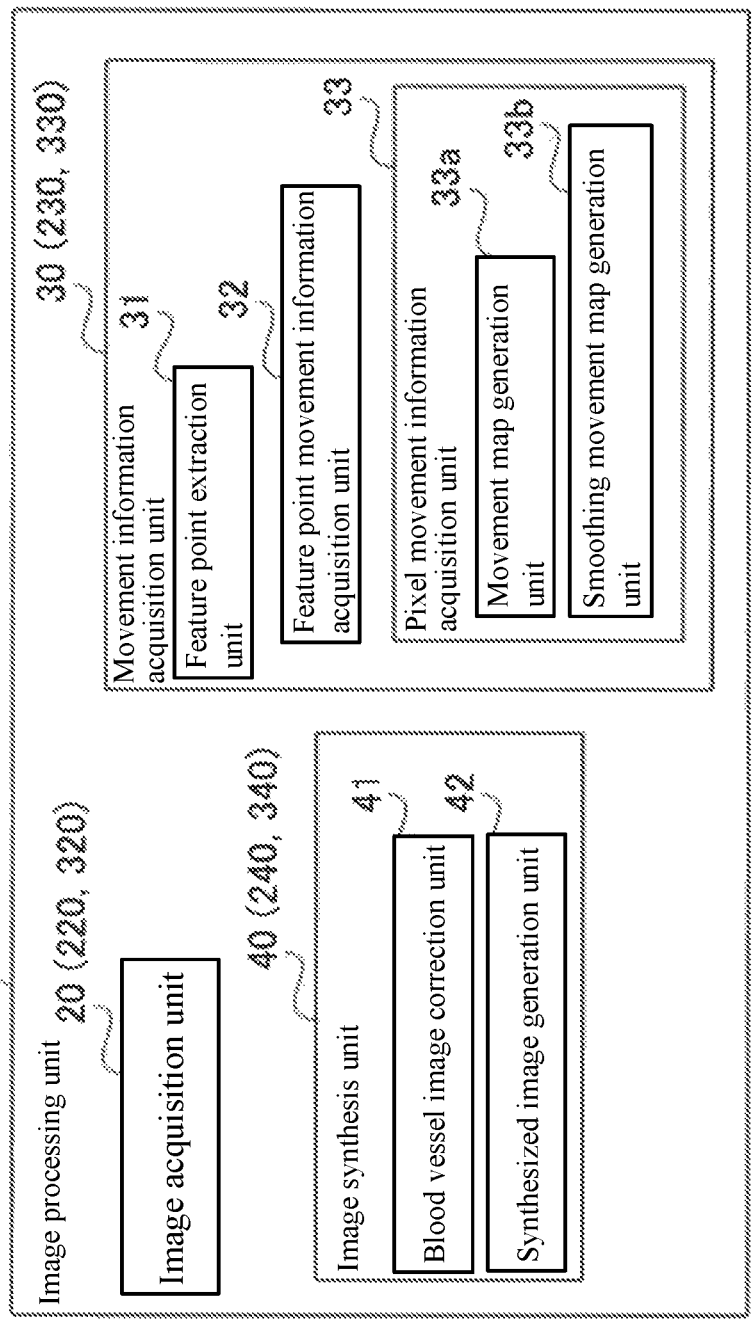
FIG. 3 is a block diagram showing the configuration of the image processing unit according to the first to third embodiments.

As shown in FIG. 3, the image processing unit 10 includes an image acquisition unit 20, a movement information acquisition unit 30, and an image synthesis unit 40. Note that although FIG. 3 illustrates the image processing unit 10 as a functional block, the present invention is not limited to this example. That is, each part of the image processing unit 10 may be configured as separate hardware (software) or as one piece of hardware (software).

<Configuration of Image Acquisition Unit>

As shown in FIG. 2, the image acquisition unit 20 is configured to acquire an X-ray image R captured by the imaging unit 2. Then, the image acquisition unit 20 is configured to acquire the X-ray image R from the imaging unit 2 as a mask image Rm, a contrast image Rc, or a live image Rr. Note that the mask image Rm is one example of the "non-contrast image" recited in claims. Also note that the live image Rr is one example of the "reference image" and the "transparent image" recited in claims. Further note that the image acquisition unit 20 is one example of the "transparent image acquisition unit" and the "reference image acquisition unit" recited in claims.

Here, in the X-ray imaging apparatus 100, the mask image Rm, the contrast image Rc, and the live image Rr are captured, for example, in this order. That is, in the X-ray imaging apparatus 100, the operation unit 6 is operated by the operator (by selecting the DSA image capturing mode). With this, the lower limb of the subject P is initially imaged in a state in which no contrast agent is administered to the blood vessel of the lower limb of the subject P (in a state in which the contrast agent does not exist in the blood vessel). Thus, the mask image Rm which is served as a mask of the DSA image Rd which will be described later is captured. Thereafter, in the X-ray imaging apparatus 100, imaging of the live image Rr is performed.

In detail, the background structural object Ab of the subject P is projected in the mask image Rm, while the blood vessel of the subject P is not clearly projected. Next, in the X-ray imaging apparatus 100, the operation unit 6 is operated by the operator to image the lower limb of the subject P in a state in which a contrast agent is administered to the blood vessel of the lower limb of the subject P (in a state in which the contrast agent remains in the blood vessel). Thus, a contrast image Rc including an image Av of the contrasted blood vessel is captured. Note that the background structural object Ab includes, for example, regions of the subject P, such as, e.g., bones and muscles. Further note that the contrast image Rc may be, for example, an image in which peak hold is applied to a plurality of X-ray images R captured consecutively.

Further, the image acquisition unit 20 is configured to generate a DSA (Digital Subtraction Angiography) image Rd by performing digital subtraction processing on the mask image Rm from the contrast image Rc. In the DSA image Rd, the background structural object Ab is substantially deleted, and the image Av of the contrast-enhanced blood vessel remains. Here, in the following description, the DSA image Rd among DSA images Rd in which the image Av remains will be described as a blood vessel image Rdb. Note that the DSA image Rd and the blood vessel image Rdb are examples of the "synthesis target image" and the "difference image" recited in claims.

After capturing the contrast image Rc and the mask image Rm, in the X-ray imaging apparatus 100, the operation unit 6 is operated by the operator (the road map transparent image capturing mode is selected) to start the imaging of the live image Rr (X-ray image R) in a state in which the irradiation dose of the X-rays from the imaging unit 2 is reduced than the irradiation dose in the imaging of the mask image Rm and the contrast image Rc. The X-ray imaging apparatus 100 is configured to capture the live image Rr sequentially in real time (as a moving image). In detail, the image acquisition unit 20 generates a live image Rr at a predetermined frame rate by imaging the X-ray detection signal sequentially output from the X-ray detection unit 2b. The frame rate is, for example, about 15 FPS to 30 FPS. The live image Rr (X-ray image R) is, for example, an image having a pixel value of a predetermined number of gradations (such as 10 to 12 bits) in grayscale.

In the first embodiment, the image acquisition unit 20 includes feature point images F1 (see FIG. 4), and acquires the first live image Rr1 which is an X-ray image R captured after the time when the mask image Rm and the contrast image Rc are captured and before the time when the second live image Rr2 is captured as a reference image. Further, the image acquisition unit 20 is configured to obtain the second live image Rr2 which is an X-ray image R captured by the imaging unit 2 to radiographically inspect the subject P and a transparent image including the feature point images F2 (see FIG. 4). Note that the first live image Rr1 is one example of the "reference image" recited in claims. Also note that the second live image Rr2 is one example of the "transparent image" recited in claims.

The mask image Rm, the contrast image Rc, and the first live image Rr1 are described as being captured at substantially the same imaging position (preferably, the same imaging position). Specifically, the "X-ray image R captured at the same imaging position" means an X-ray image R in which the positions of the feature point images F which will be described later are identical to each other (shift amount d1 is approximately 0).

In detail, when the imaging position of the first live image Rr1 is changed by the operator, based on the changed imaging position of the first live image Rr1 after the change, the DSA image Rd (mask image Rm and contrast image Rc) having the same imaging position are read out from the storage unit 4. Note that the control unit 3 is configured to acquire position information from the drive units (such as encoders) of the imaging unit 2 and the top board 1. Since this position information is associated with each X-ray image R, the image acquisition unit 20 is configured to acquire the imaging position.

The first live image Rr1 is a live image Rr at the time of image-capturing immediately after the start of the road map transparent image capturing mode (immediately after the time of capturing the contrast image Rc). For example, the first live image Rr1 is a first live image Rr after starting the road map transparent image capturing mode. That is, the first live image Rr1 is a transparent image at the time when the movement (body movement) of the subject P from the contrast image Rc substantially does not occur. Further, the second live image Rr2 is, for example, the latest (current) live image Rr. That is, the second live image Rr2 is an image captured at the time after the contrast image Rc, the mask image Rm, and the first live image Rr1. Also, the second live image Rr2 is an X-ray image R that constitutes a road map transparent image Rs.

<Structure of Movement Information Acquisition Unit>

As shown in FIG. 3, in the first embodiment, the movement information acquisition unit 30 includes a feature point extraction unit 31 for extracting the feature point image F from each of the first live image Rr1 and the second live image Rr2, a feature point movement information acquisition unit 32 for acquiring movement information E1 of the feature point based on the feature point image F extracted by the feature point extraction unit 31, and a pixel movement information acquisition unit 33 for acquiring the movement information E2 of at least some of pixels belonging to the first live image Rr1 based on the first live image Rr1 and the second live image Rr2.

Figure 4:
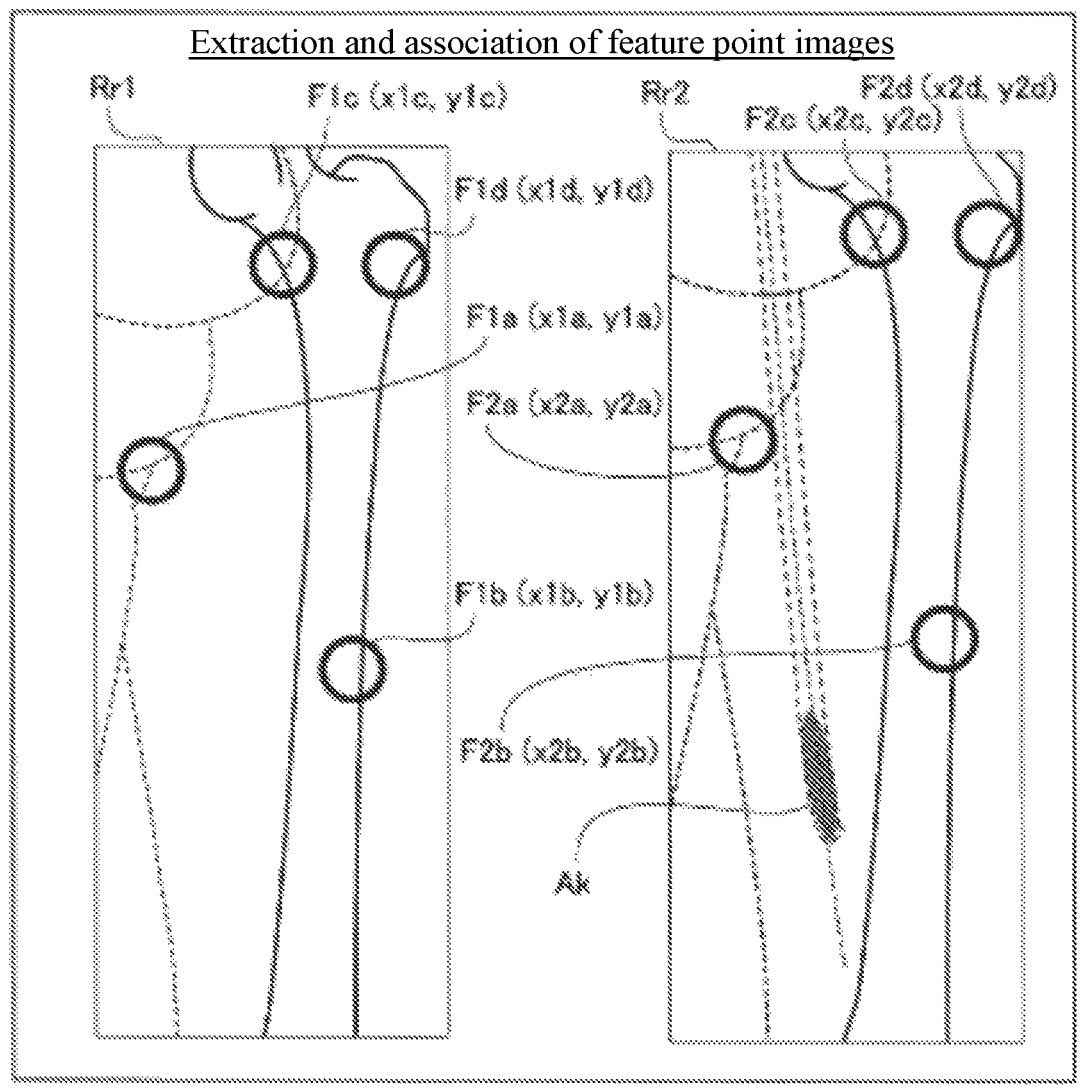
FIG. 4 is a diagram for explaining acquisition of movement information of a feature point according to the first embodiment.

Here, in the first embodiment, as shown in FIG. 4, the feature point extraction unit 31 is configured to extract a plurality of (four in FIG. 4) feature point images F1 (F1a, F1b, F1c, and F1d) from the first live image Rr1, and extract a plurality of (four in FIG. 4) feature point images F2 (F2a, F2b, F2c, and F2d) from the second live image Rr2. For example, the feature point extraction unit 31 is configured to extract an image having high similarity to the pattern image stored in the storage unit 4 or an image area whose change in luminance is larger than a predetermined change amount in the first live image Rr1 and the second live image Rr2 as feature point images F1 and F2. It should be noted that the method of extracting the feature point images F1 and F2 by the feature point extraction unit 31 is not limited to this example, and a feature point extracting method of a known image processing technique may be used.

The feature point images F1 and F2 are regions (portions enclosed by circles in FIG. 4) composed of a plurality of pixels. Although in FIG. 4, the feature point images F1 and F2 are shown in a circular shape, but not limited to a circular shape, and may have a shape other than a circular shape (for example, a rectangular shape). For example, the feature point image F1a and the feature point image F2a are images showing the same portion in the subject P. In the same manner, the feature point images F1b, F1c, and F1d are images showing portions corresponding to the feature point images F2b, F2c, and F2d, respectively.

The feature point movement information acquisition unit 32 is configured to perform processing (matching processing) of associating the feature point image F1 with the feature point image F2. For example, the feature point movement information acquisition unit 32 performs pattern matching processing on each of the feature point images F1a to F1d and the feature point images F2a to F2d to thereby associate (link) the feature point images F1a and F2a, associate the feature point images F1b and F2b, associates the feature point images F1c and F2c, and associates the feature point images F1d and F2d. For example, the feature point movement information acquisition unit 32 associates the feature point images with higher similarity among the feature point images F1a to F1d and the feature point images F2a to F2d.

Further, the feature point movement information acquisition unit 32 is configured to acquire the movement amount to the position of the subject P in the second live image Rr2 with respect to the position of the subject P in the first live image Rr1. Specifically, the feature point movement information acquisition unit 32 is configured to obtain (calculate) the mean value d1 of the movement amount from the feature point images F1a to F1d to the feature point images F2a to F2d (hereinafter referred to as "shift amount d1"). That is, the feature point movement information acquisition unit 32 is configured to calculate the shift amount d1 of the feature point due to the movement of the subject P or the position change of the imaging unit 2.

In detail, the feature point movement information acquisition unit 32 acquires the displacement da (dxa, dya) between the central coordinate (x1a, y1a) of the feature point image F1a and the central coordinate (x2a, y2a) of the feature point image F2a associated with the feature point image F1a. The feature point movement information acquisition unit 32 acquires the displacements db, dc, and dd from the feature point images F1b to F1d to the feature point images F2b to F2d in the same manner as in the displacement da. Then, the feature point movement information acquisition unit 32 acquires the mean value of the displacements da to dd as a shift amount d1. Note that the shift amount d1 is included in the movement information E1 of the feature point. Also note that "acquisition of the mean value" means not only calculating an arithmetical mean value (arithmetic mean value) but also calculating a mean value such as a weighted mean value other than an arithmetic mean value.

Further, the feature point movement information acquisition unit 32 is configured to acquire the shift amount d1 each time a new second live image Rr2 is acquired. In the first embodiment, the feature point movement information acquisition unit 32 is configured to correct the first live image Rr1 so as to move by the shift amount d1 when the shift amount d1 exceeds a threshold value d1t. That is, the feature point movement information acquisition unit 32 does not correct the first live image Rr1 when the shift amount d1 is less than the threshold value d1t. For example, the feature point movement information acquisition unit 32 is configured to generate a first corrected live image Rr1c by performing at least one of image processing of a parallel translation and a rotational movement of the first live image Rr1 by the shift amount d1 when the shift amount d1 exceeds the threshold value d1t. Note that the threshold value d1t is one example of the "movement amount threshold value" recited in claims.

The pixel movement information acquisition unit 33 is configured to acquire movement information E2 of a pixel based on a first corrected live image Rr1c and a second live image Rr2 when the first corrected live image Rr1c is generated. Further, the pixel movement information acquisition unit 33 is configured to acquire the movement information E2 of a pixel based on the first live image Rr1 and the second live image Rr2 when the first corrected live image Rr1c has not been generated. Hereinafter, "the case in which the first corrected live image Rr1c is generated" will be described, but in "the case in which the first corrected live image Rr1c has not been generated", the following description of the "first corrected live image Rr1c" shall be read as the "first live image Rr1".

Specifically, the pixel movement information acquisition unit 33 is configured to acquire the movement information E2 of a pixel for performing correction processing using a Flex-APS technology. In the first embodiment, the pixel movement information acquisition unit 33 includes a movement map generation unit 33a for acquiring a movement map M1 representing the movement direction and the movement amount of at least some of pixels belonging to the first corrected live image Rr1c based on the first corrected live image Rr1c and the second live image Rr2 and a smoothing movement map generation unit 33b for acquiring a smoothing movement map M2 in which high frequency components of the movement map M1 in the spatial direction is suppressed as movement information E2 of the pixel. In other words, the movement map M1 is a motion vector. In other words, the smoothing movement map M2 is a smoothing motion vector.

Figure 5:
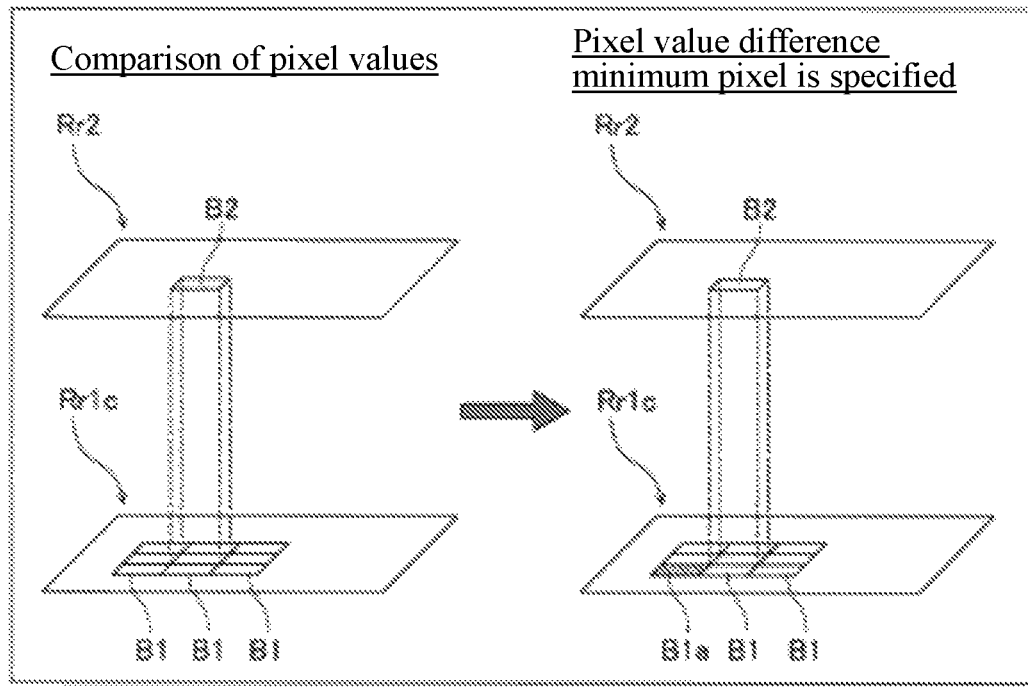
FIG. 5 is a diagram for explaining identification of a pixel value difference minimum pixel according to the first embodiment.

As shown in FIG. 5, the movement map generation unit 33a is configured to generate a movement map M1 representing the movement direction and the movement amount of the pixel B1 of the first corrected live image Rr1c based on the pixel value difference between the pixel value of the pixel B2 of the second live image Rr2 and the pixel value of the pixel B1 corresponding to the pixel B2 of the first corrected live image Rr1c and the pixel value of the pixel B1 belonging to a predetermined peripheral region. In more detail, the movement map generation unit 33a is configured to generate a movement map M1 representing the movement direction and the movement amount of the pixel B1 of the first corrected live image Rr1c based on the pixel value of the pixel B2 of the second live image Rr2 and the pixel value of the pixel value difference minimum pixel B1a which is the Pixel B1 in the First Corrected Live Image Rr1c in which the pixel value difference is smallest with respect to the pixel B2 of the second live image Rr2.

Figure 6:
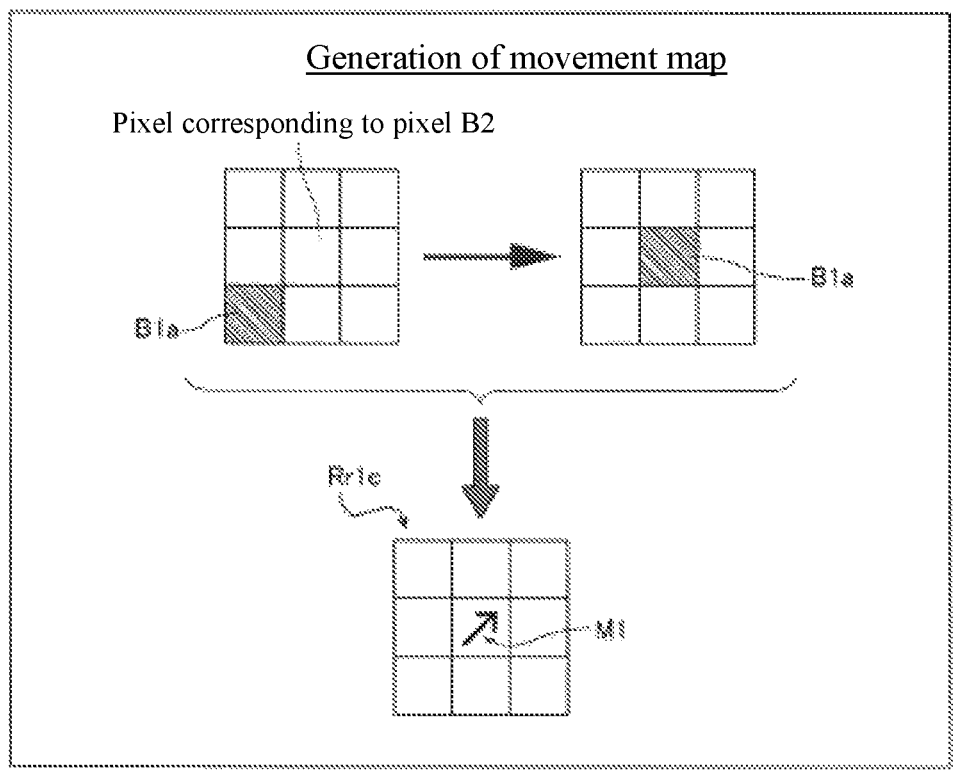
FIG. 6 is a diagram for explaining generation of a movement map according to the first embodiment.

Specifically, as shown in FIG. 6, the movement map generation unit 33a compares, by each pixel value, the pixel B2 in the second live image Rr2 with a total of nine pixels B1: a pixel B1 in the first corrected live image Rr1c corresponding to the pixel B2 (having the same coordinate); and pixels B1 in a predetermined peripheral region (a total of eight; upper, upper right, right, lower right, lower, lower left, left, upper left) of the corresponding pixel B1. Then, the movement map generation unit 33a identifies the pixel (pixel value difference minimum pixel B1a) in which the difference in pixel value from a pixel B2 of the second live image Rr2 is smallest among the nine pixels B1 of the first corrected live image Rr1c.

Here, the pixel value is a quantitative value that varies depending on the position of the subject P, and therefore it is served as an index of the position of the subject P in the second live image Rr2 and the first corrected live image Rr1c. Therefore, as described above, comparing the pixel B2 of the second live image Rr2 with nine pixels B1 in the first corrected live image Rr1c having the same coordinate as the pixel B2 and surroundings thereof corresponds to examining the positional displacement of the first corrected live image Rr1c with respect to the pixel B2 of the second live image Rr2. Also, the pixel value difference minimum pixel B1a of the first corrected live image Rr1c is a pixel which is most likely to have the positional displacement of the pixel B2 of the second live image Rr2. As shown in FIG. 6, the movement map generation unit 33a defines the movement direction and the movement amount of the pixel value difference minimum pixel B1a when the pixel value difference minimum pixel B1a is moved to the position of the pixel B1 of the first corrected live image Rr1c (which is the same coordinate) corresponding to the pixel B2 of the second live image Rr2 as a movement map M1 corresponding to the pixel B1 of the first corrected live image Rr1c.

Figure 7:
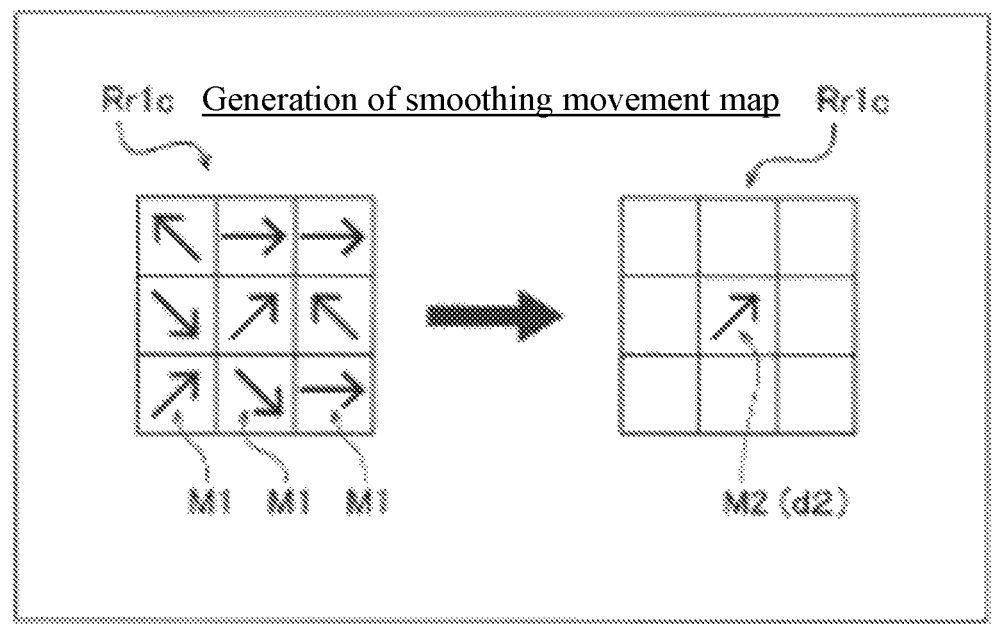
FIG. 7 is a diagram for explaining generation of the smoothing movement map according to the first embodiment.

As shown in FIG. 7, the smoothing movement map generation unit 33b is configured to generate a smoothing movement map M2 by suppressing high frequency components of the movement map M1 in the spatial direction. Specifically, the smoothing movement map generation unit 33b calculates a smoothing movement map M2 in which the movement map M1 is smoothed with the pixel B1 in the first corrected live image Rr1c and the pixels B1 around the pixel B1 in the first corrected live image Rr1c for each pixel B1 in the first corrected live image Rr1c. That is, the smoothing movement map generation unit 33b calculates a smoothing movement map M2 in which the movement map M1 associated with each pixel B1 in the first corrected live image Rr1c is smoothed with the pixel B1 and eight surrounding pixels B1. Note that smoothing means, for example, averaging movement maps M1 at nine pixels B1.

Figure 8:
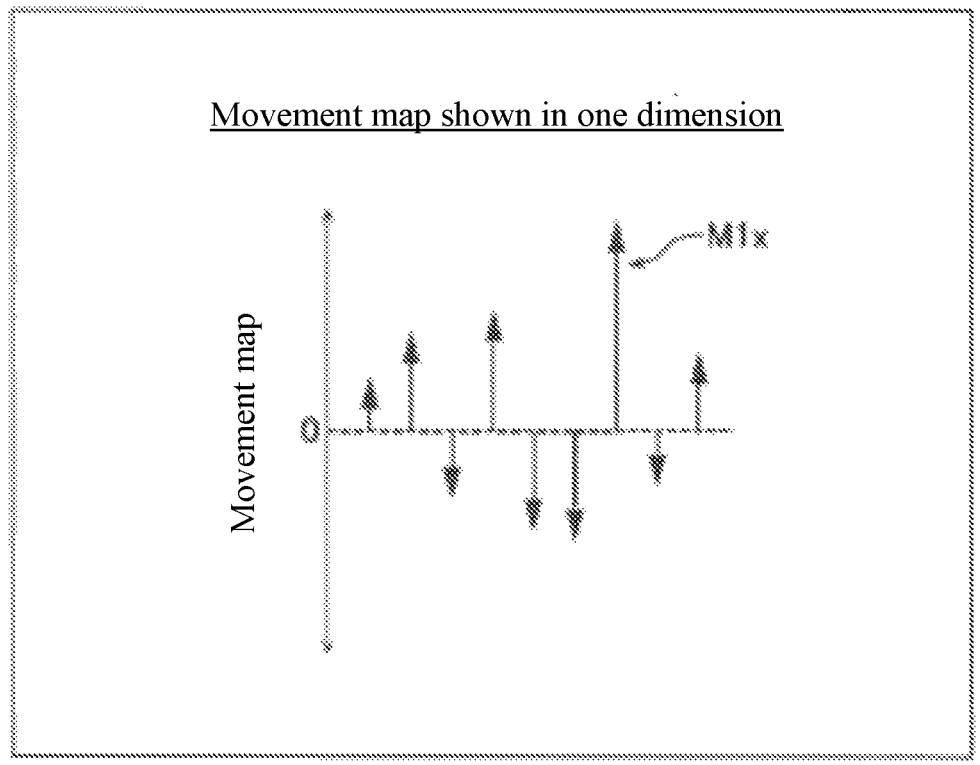
FIG. 8 is a diagram for explaining a movement map shown in one dimension according to the first embodiment.

By performing the smoothing, as shown in FIG. 8, even in cases where a movement map (movement map M1x) which is excessively different in movement map M1 is included in the nine pixels B1, the movement maps M1 are averaged, and therefore the influence of the excessively different movement map M1x is reduced. As a result, the high frequency components of the movement map M1 in the spatial direction are suppressed. Note that, in FIG. 7, the smoothing movement map M2 is drawn by the vector of the same direction and magnitude as the movement map M1 before smoothing due to limitations of space. Note that the smoothing is not limited to the case of simply averaging the movement maps M1 with the nine pixels B1. For example, after graphing the movement maps M1 of the nine pixels B1 with the movement amount for each movement direction, high frequency components may be extracted by performing Fourier transform. Then, by removing the high frequency components, the high frequency components of the movement map M1 in the spatial direction may be suppressed.

Then, the smoothing movement map generation unit 33b associates the generated smoothing movement map M2 with the pixel B1 of the first corrected live image Rr1c corresponding to the pixel B2 of the second live image Rr2. Then, the smoothing movement map generation unit 33b performs this association on all the pixels B1 of the first corrected live image Rr1c, whereby the smoothing movement map M2 becomes in a state of being associated with all the pixels B1 of the first corrected live image Rr1c. In the first embodiment, the information of the movement amount d2 of the first corrected live image Rr1c in which the smoothing movement map M2 is associated with all the pixels B1 of the first corrected live image Rr1c is the movement information E2 of pixels, and this movement amount d2 is used for the correction of the DSA image Rd.

<Configuration of Image Synthesis Unit>

As shown in FIG. 3, the image synthesis unit 40 includes: a blood vessel image correction unit 41 that corrects a DSA image Rd (blood vessel image Rdb) captured at the same imaging position as the first live image Rr1 based on the movement information E1 (shift amount d1) of the feature point and the movement information E2 (movement amount d2) of the pixel to generate a corrected blood vessel image Rdbc (black and white inverted image Ava); and a synthesized image generation unit 42 that synthesizes the generated corrected blood vessel image Rdbc and the second live image Rr2 to generate a road map transparent image Rs. Note that the corrected blood vessel image Rdbc and the black and white inverted image Ava are examples of the "inverted image" recited in claims.

As shown in FIG. 2, the blood vessel image correction unit 41 is configured to read out the blood vessel image Rdb from the DSA image Rd stored in the storage unit 4. Then, the blood vessel image correction unit 41 performs (at least one of parallel translation or rotational movement) processing of moving the position of the blood vessel image Rdb (the position of the image Av) by the shift amount d1 with respect to the position before correction. Further, the blood vessel image correction unit 41 performs processing of moving a part (for example, every pixel or every predetermined area) and the entire image (entire image Av or entire DSA image Rd) by the movement amount d2.

In the first embodiment, the blood vessel image correction unit 41 is configured to generate a corrected blood vessel image Rdbc in which the blood vessel image Rdb corrected based on the movement information E1 of the feature point and the movement information E2 of the pixel is subjected to black and white inversion processing. Specifically, the blood vessel image correction unit 41 performs the black and white inversion processing (processing to reverse the luminance) on the corrected blood vessel image Rdbc which has been moved by the shift amount d1 and moved by the movement amount d2 to generate a corrected blood vessel image Rdbc including a black and white inverted image Ava.

The blood vessel image correction unit 41 is configured to correct the blood vessel image Rdb (DSA image Rd) based on the movement information E1 of the feature point and the movement information E2 of the pixel every time a new second live image Rr2 is acquired by the image acquisition unit 20. That is, the blood vessel image correction unit 41 is configured to correct the blood vessel image Rdb sequentially in real time to generate a corrected blood vessel image Rdbc.

The synthesized image generation unit 42 is configured to synthesize the corrected blood vessel image Rdbc and the second live image Rr2 to generate a road map transparent image Rs. Specifically, the synthesized image generation unit 42 is configured to generate a road map transparent image Rs so that the corrected blood vessel image Rdbc and the second live image Rr2 are displayed in a superimposed manner. Further, the synthesized image generation unit 42 is configured to correct the blood vessel image Rdb to generate a corrected blood vessel image Rdbc based on the movement information E1 of the feature point and the movement information E2 of the pixel every time a new second live image Rr2 is acquired by the image acquisition unit 20, and generate a road map transparent image Rs by synthesizing the generated corrected blood vessel image Rdbc and the second live image Rr2.

In other words, in the first embodiment, the synthesized image generation unit 42 is configured to acquire a DSA image Rd which is a difference image between the contrast image Rc which is an X-ray image R in a state in which a contrast agent has been administered to the blood vessel of the lower limb of the subject P and the mask image Rm which is an X-ray image R in a state in which no contrast agent has been administered to the blood vessel of the subject P, correct the blood vessel image Rdb to a corrected blood vessel image Rdbc based on the movement information E1 of the feature point and the movement information E2 of the pixel, and synthesize the corrected blood vessel image Rdbc and the second live image Rr2 to generate a road map transparent image Rs.

Thus, in the first embodiment, the synthesized image generation unit 42 is configured to generate a road map transparent image Rs by synthesizing the corrected blood vessel image Rdbc and the second live image Rr2 including the image Ak in which at least one of a catheter, a stent, and a guide wire inserted in the subject P is projected. The road map transparent image Rs is displayed by the display unit 5, and is visually recognized by the operator.

(X-Ray Image Processing Method)

Figure 9:
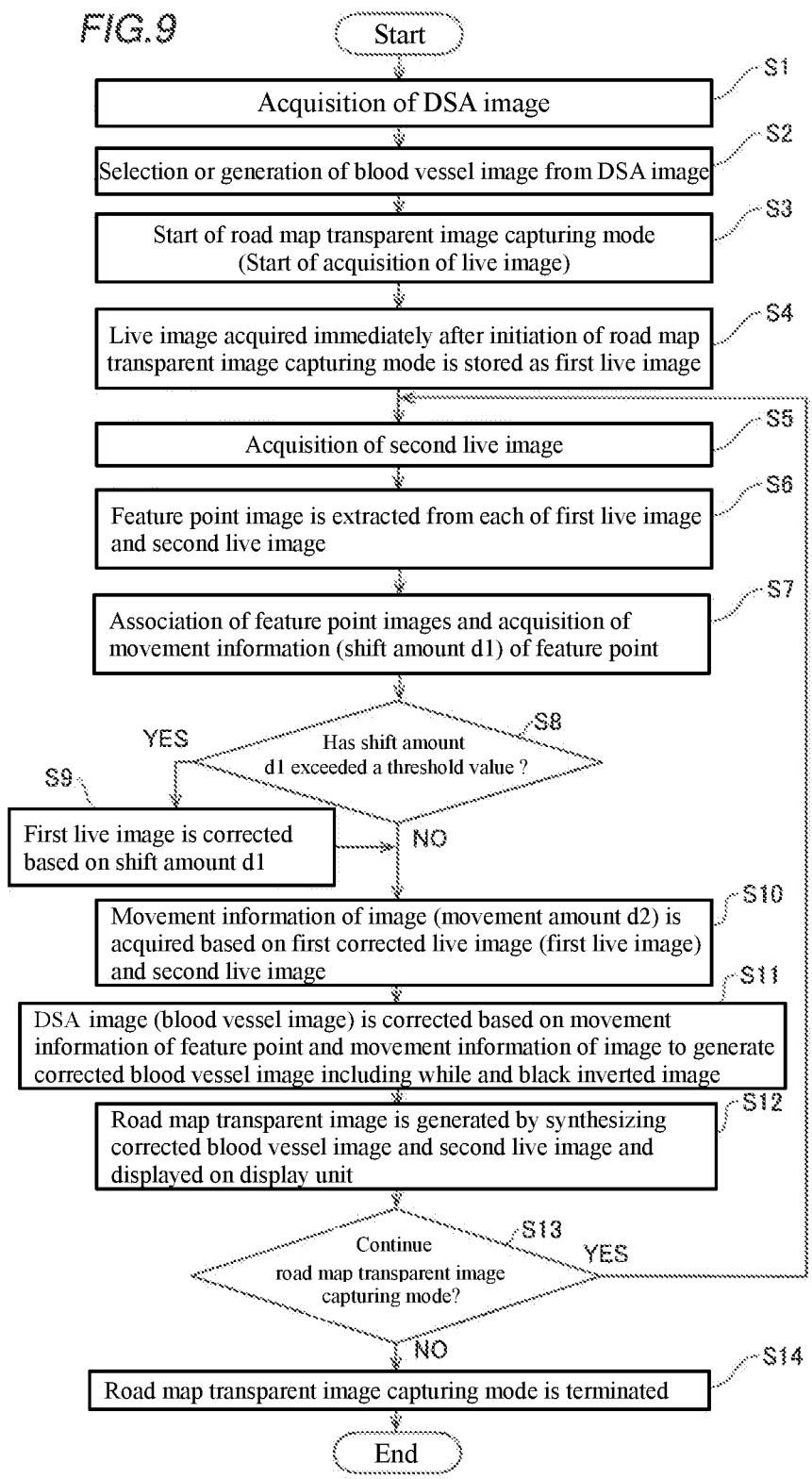
FIG. 9 is a diagram (flowchart) showing a flow of the control processing in the X-ray imaging apparatus according to the first embodiment.

Next, with reference to FIG. 9, the control processing (X-ray image processing method) of the X-ray image R by the X-ray imaging apparatus 100 according to the first embodiment will be described. FIG. 9 shows the flow of the control processing of the X-ray image R by the X-ray imaging apparatus 100. The control processing of the X-ray image R by the X-ray imaging apparatus 100 is executed by the control unit 3 (image processing unit 10).

First, in Step S1, acquisition of a DSA image Rd is performed in a DSA image capturing mode. That is, a mask image Rm and a contrast image Rc are captured (acquired), and a DSA image Rd is generated based on the mask image Rm and the contrast image Rc.

In Step S2, selection (generation) of the blood vessel image Rdb is performed from the DSA image Rd. For example, the blood vessel image Rdb is selected from the DSA image Rd stored in storage unit 4 by an input operation for the operation unit 6 or automatically.

In step S3, in accordance with the input operation of the operation unit 6 by the operator, the road map transparent image capturing mode is started, and acquisition of the live image Rr is started.

In Step S4, the live image Rr immediately after the start of the road map transparent image capturing mode is held as a first live image Rr1. That is, the road map transparent image capturing mode is started, and the live image Rr to be acquired first is stored as the first live image Rr1 in the storage unit 4 or the image processing unit 10.

In Step S5, the live image Rr captured after the first live image Rr1 is acquired as a second live image Rr2.

In Step S6, a feature point image F is extracted from each of the first live image Rr1 and the second live image Rr2. For example, as shown in FIG. 4, the feature point images F1$a$ to F1$d$ are extracted from the first live image Rr1, and the feature point images F2$a$ to F2$d$ are extracted from the second live image Rr2.

In Step S7, the movement information E1 (shift amount d1) of the feature point is acquired. Specifically, as shown in FIG. 4, association (matching processing) of the feature point images F1$a$ to F1$d$ of the first live image Rr1 and the feature point images F2$a$ to F2$d$ of the second live image Rr2 is performed, and the mean value (shift amount) d1 of each of the displacements da to dd is obtained (calculated). That is, the shift amount d1 of the feature point due to the movement of the subject P or the position change of the imaging unit 2 is calculated.

In Step S8, it is determined whether or not the shift amount d1 has exceeded the threshold value d1$t$. That is, the shift amount d1 and the threshold value d1$t$ are compared, and when the shift amount d1 exceeds the threshold value d1$t$, the process proceeds to Step S9, and when the shift amount d1 does not exceed the threshold value d1$t$, the process proceeds to Step S10.

In Step S9, the first live image Rr1 is corrected based on the shift amount d1, and a first corrected live image Rr1$c$ is generated. Thereafter, the process proceeds to Step S10.

In Step S10, the movement information E2 (movement amount d2) of the image is acquired based on the first corrected live image Rr1$c$ and the second live image Rr2. That is, the movement map M1 shown in FIG. 5 to FIG. 8 is acquired, and the smoothing movement map M2 is acquired as movement information E2 (movement amount d2) of the image.

In Step S11, based on the movement information E1 (shift amount d1) of the feature point and the movement information E2 (movement amount d2) of the pixel, the DSA image Rd (blood vessel image Rdb) is corrected to generate a corrected blood vessel image Rdbc including the black and white inverted image Ava.

In Step S12, the corrected blood vessel image Rdbc and the second live image Rr2 are synthesized, a road map transparent image Rs is generated, and the road map transparent image Rs is displayed on the display unit 5.

In Step S13, it is determined whether to continue the road map transparent image capturing mode. For example, when the operation unit 6 has not received the input operation for ending the road map transparent image capturing mode, the process returns to Step S5 so as to continue the road map transparent image capturing mode. When the operation unit 6 has received an input operation for ending the road map transparent image capturing mode, the process proceeds to Step S14 so as to not continue (so as to end) the road map transparent image capturing mode. That is, when the road map transparent image capturing mode is continued, Steps S5 to S13 are repeated, and each time a second live image Rr2 is acquired, based on the movement information E1 of the feature point and the movement information E2 of the pixel, the blood vessel image Rdb is corrected, and a road map transparent image Rs is generated in which the corrected blood vessel image Rdb which is a corrected blood vessel image Rdbc and the second live image Rr2 are synthesized.

In Step S14, the road map transparent image capturing mode is ended. Thereafter, the control processing of the X-ray image R by the X-ray imaging apparatus 100 is ended.

Effects of First Embodiment

In the first embodiment, the following effects can be obtained.

In the first embodiment, as described above, the movement information acquisition unit 30 is configured to acquire the movement information E1 of the feature point and acquire the movement information E2 of the pixel based on the feature point image F1 of the first live image Rr1 which is an X-ray image R captured before the time when the second live image Rr2 is captured and the feature point image F2 of the second live image Rr2. And, the image synthesis unit 40 is configured to correct the DSA image Rd (blood vessel image Rdb) captured at an imaging position substantially the same as the first live image Rr1 based on the movement information E1 of the feature point and the movement information E2 of the pixel and synthesize the corrected DSA image Rd (corrected blood vessel image Rdbc) and the second live image Rr2 to generate a road map transparent image Rs.

With this, even in cases where the subject P has moved with respect to the imaging unit 2 after capturing the DSA image Rd (blood vessel image Rdb) and the first live image Rr1, the DSA image Rd (blood vessel image Rdb) can be corrected so as to come alignment with the position of the subject P at the time when the second live image Rr2 is captured. For this reason, it can be suppressed that the X-ray images R (the DSA image Rd (blood vessel image Rdb) and the second live image Rr2) of the subject P whose positions are shifted from one another are synthesized. As a result, even in cases where the subject has moved after capturing the synthesis target image when synthesizing the DSA image Rd (blood vessel image Rdb) and the second live image Rr2 (X-ray image R) captured at different time points to generate a road map transparent image Rs, a road map transparent image Rs can be generated appropriately (the positional displacement between images is suppressed). This eliminates the necessity of re-capturing a DSA image Rd (blood vessel image Rdb), which makes it possible to suppress an increase in the radiation exposure of X-rays with respect to the subject P.

Further, in the first embodiment, as described above, the movement information acquisition unit 30 is configured to acquire the movement information E1 of the feature point and the movement information E2 of the pixel as information for correcting the DSA image Rd (blood vessel image Rdb).

With this, the movement information E1 of the feature point is obtained as relatively broad range (macro) movement information in the first live image Rr1 and the second live image Rr2, and therefore a correction with respect to a relatively broad movement (relatively large movement) of the subject P can be made. And, the movement information E2 of the pixel is obtained as relatively narrow range (micro) movement information in the first live image Rr1 and the second live image Rr2, and therefore a correction with respect to the relatively narrow movement (relatively small movement) of the subject P can be made. As a result of these, it is possible to correct the DSA image Rd (blood vessel image Rdb) more appropriately by performing both of the correction for the relatively large movement of the subject P and the correction for the relatively small movement of the subject P, which mutually complement advantages and disadvantages. Therefore, even in the case of synthesizing the DSA image Rd (blood vessel image Rdb) and the X-ray image R captured at different time points with each other to generate a road map transparent image Rs, it is possible to more appropriately generate a road map transparent image Rs (the positional displacement between images is further suppressed).

In the first embodiment, as described above, the image acquisition unit 20 is configured to acquire the second live image Rr2 as a live image Rr which is sequentially generated in real time. Further, the image synthesis unit 40 is configured to synthesize the corrected DSA image Rd (corrected blood vessel image Rdbc) and the live image Rr to generate a road map transparent image Rs. With this, since it is possible to correct the DSA image Rd (blood vessel image Rdb) corresponding to the change of the live image Rr, even in cases where the DSA image Rd is synthesized with the live image Rr which is displayed in real time and changes sequentially, a road map transparent image Rs can be generated appropriately.

Also, in the first embodiment, as described above, the image synthesis unit 40 is configured to correct the DSA image Rd (blood vessel image Rdb) based on the movement information E1 of the feature point and the movement information E2 of the pixel every time the live image Rr is acquired by the image acquisition unit 20. Further, the image synthesis unit 40 is configured to synthesize the corrected DSA image Rd (corrected blood vessel image Rdbc) and the live image Rr to generate a road map transparent image Rs.

This makes it possible to correct the DSA image Rd (blood vessel image Rdb) so as to be updated sequentially in correspondence with the live image Rr to be updated. For this reason, even in the case of synthesizing the DSA image Rd (blood vessel image Rdb) with the live image Rr (for example, video) that changes sequentially, it is possible to generate a road map transparent image Rs (in which the positional displacement between images is suppressed) more appropriately. As a result, even in cases where the operator performs a medical treatment of the subject P while visually recognizing the road map transparent image Rs displayed as a moving image, a road map transparent image Rs in which the positional displacement is more effectively suppressed can be generated.

Further, in the first embodiment, as described above, the image synthesis unit 40 is configured to acquire the difference image between the contrast image Rc which is an X-ray image R in a state in which a contrast agent has been administered to the blood vessel of the lower limb of the subject P and the mask image Rm which is an X-ray image R in a state in which no contrast agent has been administered to the blood vessel of the subject P as a DSA image Rd (blood vessel image Rdb). Further, the image synthesis unit 40 is configured to correct the DSA image Rd (blood vessel image Rdb) based on the movement information E1 of the feature point and the movement information E2 of the pixel and synthesize the corrected DSA image Rd (corrected blood vessel image Rdbc) and the second live image Rr to generate a road map transparent image Rs.

With this, when the operator performs various medical treatments by inserting a catheter into the lower limb blood vessel of the subject P, it is possible to provide an X-ray imaging apparatus 100 capable of generating a road map transparent image Rs in which the positional displacement between images is effectively suppressed.

Further, in the first embodiment, as described above, the image synthesis unit 40 is configured to synthesize the black and white inverted image Ava in which the image Av of the contrasted blood vessel of the corrected blood vessel image Rdbc corrected based on the movement information E1 of the feature point and the movement information E2 of the pixel is subjected to the black and white inversion processing to generate a road map transparent image Rs.

With this, in the DSA image Rd, a substantially black image (blood vessel image Rdb) is synthesized with the live image Rr in a state of being converted to a substantially white image (for example, a black and white inverted image Ava), and therefore the therapeutic device (for example, a catheter, a stent, a guide wire, etc.) in the portion corresponding to the blood vessel in the live image Rr can be displayed in black (a color different from the black and white inverted image Ava). As a result, it is possible to make the operator visually recognize the appropriately enhanced image of the blood vessel while improving the visibility of the portion (therapeutic device) corresponding to the blood vessel in the live image Rr.

Further, in the first embodiment, as described above, the image synthesis unit 40 is configured to synthesize the black and white inverted image Ava and the live image Rr including the image Ak in which at least one of a catheter, a stent, and a guide wire inserted in the subject P is projected to generate a road map transparent image Rs. With this, it is possible to make the operator recognize the image of the blood vessel which is projected as an approximate background color (white) by the black and white inversion processing and the image Ak in which at least one of a catheter, a stent, and a guide wire inserted in the subject P is projected in a manner as to be more easily distinguished.

Further, in the first embodiment, as described above, the movement information acquisition unit 30 is configured to acquire the live image Rr captured before the second live image Rr2 as the first live image Rr1 at the imaging position substantially the same as the imaging position of the contrast image Rc and the mask image Rm. With this, between the live images Rr in which the X-ray irradiation dose is almost equal to each other, the feature point images F1a to F1d of the first live image Rr1 (live image Rr) and the feature point image F2a to F2d of the second live image Rr2 (live image Rr) can be associated with each other. This makes it possible to correct the DSA image Rd (blood vessel image Rdb) while suppressing complication of the control processing at the time of association since the control processing for correcting the luminance is unnecessary.

Further, in the first embodiment, as described above, the movement information acquisition unit 30 is configured to correct the first live image Rr1 based on the movement information E1 of the feature point and acquire the movement information E2 of the pixel based on the corrected first live image Rr1 and the second live image Rr2 when the shift amount d1 from the feature point image F of the first live image Rr1 to the feature point image F of the second live image Rr2 has exceeded a threshold value d1$t$.

With this, when the position of the feature point has moved relatively largely with respect to the imaging unit 2 by the relatively large movement of the subject P (when the shift amount d1 has exceeded the threshold value d1$t$), the first live image Rr1 can be corrected based on the movement information E1 of the feature point. For example, when the movement of the subject P is relatively small (when the shift amount d1 does not exceed the threshold valued d1$t$), by correcting the DSA image Rd (blood vessel image Rdb) based on the movement information E2 of the pixel without performing the control processing to correct the first live image Rr1 (only by correcting the relatively small movement of the subject P), the road map transparent image Rs can be generated appropriately while reducing the control load of the image synthesis unit 40.

Further, in the first embodiment, as described above, the movement information acquisition unit 30 is configured to extract a plurality of feature point images F1a to F1d from the first live image Rr1, extract a plurality of feature point images F2a to F2d from the second live image Rr2, and correct the first live image Rr1 so as to move the first live image Rr1 by the mean value (by the shift amount d1) of the movement amount of the first live image Rr1 from the feature point image F1a to F1d to the feature point images F2a to F2d of the second live image Rr2. Then, the movement information acquisition unit 30 is configured to acquire the movement information E2 of the pixel based on the first corrected live image Rr1$c$ and the second live image Rr2.

With this, since the first live image Rr1 is corrected based on the means value of the plurality of movement amounts (displacements da to dd), compared with the case in which the movement amount of only one feature point is used, it is possible to more accurately obtain the information on the movement of the entire subject P reflected in the first live image Rr1 and the second live image Rr2.

In the first embodiment, as described above, the movement information acquisition unit 30 is configured to acquire the movement map M1 representing the movement direction and the movement amount of at least some of pixels B1 belonging to the first live image Rr1 based on the first live image Rr1 and the second live image Rr2 and acquire the smoothing movement map M2 in which the high frequency components of the movement map M1 in the spatial direction is suppressed as the movement information E2 of the pixel.

With this, by acquiring the smoothing movement map M2 in which the high frequency components of the movement map M1 in the spatial direction is suppressed as the movement information E2 of the pixel, even if an error occurs in the movement map M1 due to the generation of the movement map M1 for each pixel B1, the influence of the error can be reduced by suppressing the high frequency components in the spatial direction. As a result, in consideration of not only the linear operation of the subject P between two X-ray images R captured at different time points but also the nonlinear operation (relatively complex operation), the DSA image Rd (blood vessel image Rdb) and the second live image Rr2 can be appropriately synthesized.

Second Embodiment

Next, the configuration of the X-ray imaging apparatus 200 according to a second embodiment of the present invention will be described with reference to FIG. 1, FIG. 3, and FIG. 10. In the second embodiment, unlike the X-ray imaging apparatus 100 according to the first embodiment which is configured to acquire the movement information E1 of the feature point and the movement information E2 of the pixel based on the first live image Rr1 and the second live image Rr2, it is configured to obtain the movement information E11 of the feature point and the movement information E12 of the pixel based on the contrast image Rc and the live image Rr12.

The same reference numerals are allotted to the same configurations as those of the first embodiment in the drawings, and the description thereof will be omitted by allotting the same reference number. Note that in the second embodiment, the contrast image Rc is one example of the "reference image" recited in claims, and the live image Rr12 is one example of the "transparent image" recited in claims.

The X-ray imaging apparatus 200 according to the second embodiment is provided with a control unit 203 having an image processing unit 210 as shown in FIG. 1. As shown in FIG. 3, the image processing unit 210 includes an image acquisition unit 220, a movement information acquisition unit 230, and an image synthesis unit 240. In the second embodiment, the image acquisition unit 220 is configured to acquire a contrast image Rc as a reference image.

Figure 10:
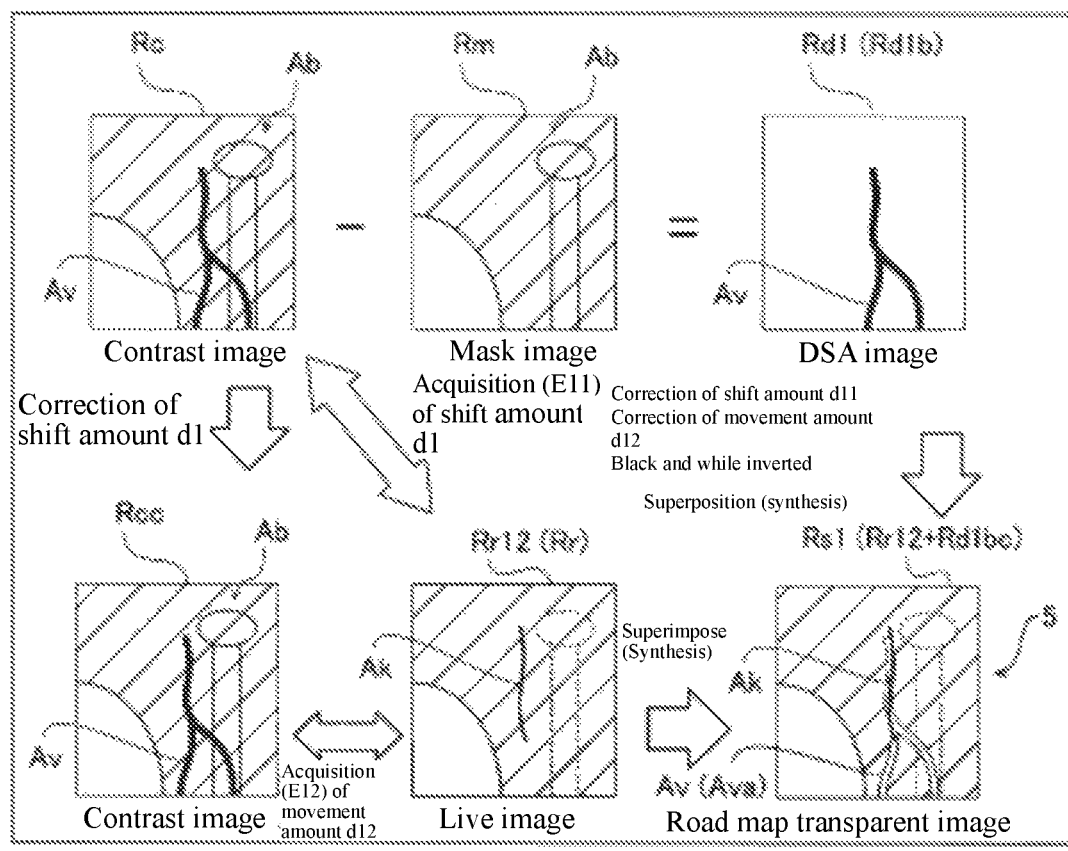
FIG. 10 is a diagram for explaining acquisition of the shift amount of the X-ray imaging apparatus, acquisition of the movement amount, and generation of the road map transparent image according to the second embodiment.

As shown in FIG. 10, the movement information acquisition unit 230 is configured to extract the feature point images from each of the contrast image Rc and the live image Rr12 and acquire the movement information E11 (shift amount d11) of the feature point based on the extracted feature point image. And the movement information acquisition unit 230 is configured to generate a corrected contrast image Rcc in which the contrast image Rc is corrected based on the movement information E11 of the feature point and acquire the movement information E12 (movement amount d12) of at least some of the pixels belonging to the corrected contrast image Rcc based on the corrected contrast image Rcc and the live image Rr12.

The image synthesis unit 240 is configured to correct the DSA image Rd1 (blood vessel image Rd1*b*) to generate the corrected blood vessel image Rd1*bc* based on the movement information E11 of the feature point and the movement information E12 of the pixel and generate the road map transparent image Rs1 by synthesizing the corrected blood vessel image Rd1*bc* and the live image Rr12. The other configurations of the second embodiment are the same as those of the first embodiment.

[Effects of Second Embodiment]

In the second embodiment, the following effects can be obtained.

In the second embodiment, as described above, the image acquisition unit 220 is configured to acquire the contrast image Rc as a reference image. Then, the movement information acquisition unit 230 is configured to extract the feature point images from each of the contrast image Rc and the live image Rr12 and acquire the movement information E11 (shift amount d11) of the feature point based on the extracted feature point image.

As a result, the contrast image Rc which is an image including the image Av of the contrasted blood vessel, and the image Ava of the blood vessel of the corrected blood vessel image Rd1*bc* are captured at the same time. Therefore, a more accurately corrected blood vessel image Rd1*bc* can be generated as compared with the case of acquiring a feature point image from a live image Rr captured at a time later than the contrast image Rc. Note that the other effects of the second embodiment are the same as those of the first embodiment.

Third Embodiment

Next, the configuration of the X-ray imaging apparatus 300 according to a third embodiment of the present invention will be described with reference to FIG. 1, FIG. 3, and FIG. 11. In the third embodiment, unlike the X-ray imaging apparatus 100 according to the first embodiment which is configured to acquire the movement information E1 of the feature point and the movement information E2 of the pixel based on the first live image Rr1 and the second live image Rr2, it is configured to acquire the movement information E21 of the feature point and the movement information E22 of the pixel based on the mask image Rm and the live image Rr22.

The same reference numerals are allotted to the same configurations as those of the first or second embodiment in the drawings, and the description thereof will be omitted. Note that in the third embodiment, the mask image Rm is one example of the "reference image" and the "non-contrast image" recited in claims, and the live image Rr22 is one example of the "transparent image" recited in claims.

The X-ray imaging apparatus 300 according to the third embodiment is provided with a control unit 303 having an image processing unit 310 as shown in FIG. 1. As shown in FIG. 3, the image processing unit 310 includes an image acquisition unit 320, a movement information acquisition unit 330, and an image synthesis unit 340. In the third embodiment, the image acquisition unit 320 is configured to acquire the mask image Rm as a reference image.

Figure 11:
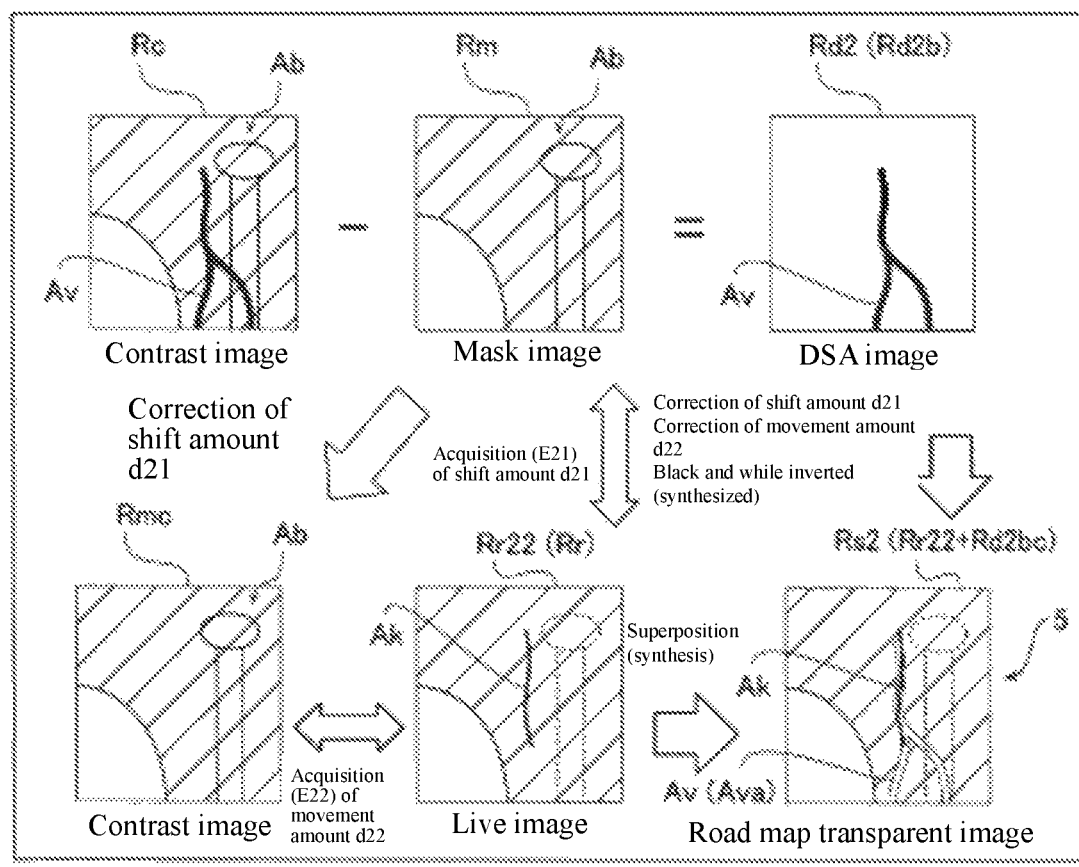
FIG. 11 is a diagram for explaining acquisition of the shift amount of the X-ray imaging apparatus, acquisition of the movement amount, and generation of the road map transparent image according to the third embodiment.

As shown in FIG. 11, the movement information acquisition unit 330 is configured to extract the feature point images from each of the mask image Rm and the live image Rr22 and acquire the movement information E21 (shift amount d21) of the feature point based on the extracted feature point image. And the movement information acquisition unit 330 is configured to generate a corrected mask image Rmc in which the mask image Rm is corrected based on the movement information E21 of the feature point and acquire the movement information E22 (movement amount d22) of at least some of the pixels belonging to the corrected mask image Rmc based on the corrected mask image Rmc and the live image Rr22.

The image synthesis unit 340 is configured to correct the DSA image Rd2 (blood vessel image Rd1*b*) to correct the DSA image Rd2 (blood vessel image Rd2*b*) based on the movement information E21 of the feature point and the movement information E22 of the pixel to generate the corrected blood vessel image Rd2*bc* and synthesize the corrected blood vessel image Rd2*bc* and the live image Rr22 to generate the road map transparent image Rs2. The other configurations of the third embodiment are the same as those of the first embodiment.

Effects of Third Embodiment

In the third embodiment, the following effects can be obtained.

In the third embodiment, the image acquisition unit 320 is configured to acquire the mask image Rm as a reference image. Then, the movement information acquisition unit 330 is configured to extract the feature point images from each of the mask image Rm and the live image Rr22 and acquire the movement information E21 (shift amount d21) of the feature point based on the extracted feature point image.

This makes it possible to suppress extraction of the feature points different from each other between the mask image Rm and the live image Rr22 which do not include the image of the contrasted blood vessel. As a result, since the feature points can be easily associated with each other, the movement information E21 of the feature point can be easily obtained. In addition, since in the mask image Rm, the radiation dose of X-rays can be increased as compared with the live image Rr, the feature point image can be extracted from the mask image Rm and the live image Rr22 which are relatively sharp. The other effects of the third embodiment are the same as those of the first embodiment.

Modified Embodiment

It should be understood that the embodiments disclosed here are examples in all respects and are not restrictive. The scope of the present invention is shown by the scope of claims rather than the descriptions of the embodiments described above, and includes all changes (modifications) within the meaning of equivalent and the scope of claims.

For example, in the above-described embodiment, as the synthesis target image of the present invention, although an example using the DSA image and the blood vessel image is shown, the present invention is not limited thereto. That is, an X-ray image that is not a DSA image may be used as a synthesis target image, or an X-ray image not including an image of a blood vessel may be used as a synthesis target image.

Also, in the above-described embodiment, although the X-ray image captured at the "same imaging position" has been described as meaning that the positions of the feature point images are identical to each other, the present invention is not limited to this. For example, the "same imaging position" may be used as meaning that the relative position of the top board with respect to the imaging unit is the same and that the relative position between the X-ray generation unit and the X-ray detection unit in the imaging unit is the same.

In the above-described embodiments, an example is shown in which the road map transparent image is generated so as to display the DSA image (blood vessel image) and the second live image in a superimposed manner, but the present invention is not limited to this. For example, a synthesized image synthesized so as to display the contrast image and the live image in parallel may be generated.

In the above-described embodiments, an example is shown in which the DSA image (blood vessel image) is corrected each time the second live image is acquired (captured), but the present invention is not limited to this. For example, the DSA image (blood vessel image) may be corrected only when an input operation for the operation unit by an operator is accepted.

Further, in the above-described embodiments, although an example is shown in which the lower limb of the subject is imaged, the present invention is not limited to this. That is, the X-ray imaging apparatus of the present invention is particularly effective in imaging a lower limb of a subject, and it exerts an effect capable of appropriately generating a synthesized image even when radiographing a region other than the lower limb of the subject.

In the above-described embodiment, an example of black and white inversion processing of the blood vessel image is shown when synthesizing the DSA image (blood vessel image) and the second live image, but the present invention is not limited thereto. That is, the blood vessel image may be synthesized with the second live image without performing the black and white inversion, or the blood vessel image may be synthesized with the second live image by performing the image processing (color change processing) other than a black and white inversion.

Furthermore, in the above-described embodiment, an example is shown in which the mean value (shift amount) of the displacements of all feature point images is obtained as the movement information of the feature points, but the present invention is not limited to this. That is, a displacement may be acquired for only some of the feature point images among the plurality of feature point images, and the shift amount may be acquired based on this displacement.

Also, in the above-described embodiment, an example is shown in which a black and white inverted image and a live image including an image in which at least one of a catheter, a stent, and a guide wire inserted in the subject is projected are synthesized, but the present invention is not limited to this. That is, a black and white inverted image and a live image including an image of a therapeutic device other than a catheter, a stent, and a guide wire may be synthesized.

Further, in the above-described embodiment, although an example is shown in which the first live image (contrast image or mask image) is corrected based on the movement information of the feature point when the shift amount has exceeded the threshold value, the present invention is not limited to this. That is, if there are few problem with the increase in a control burden, without setting a threshold value, each time a live image is acquired, the first live image (contrast image or mask image) may be corrected based on the movement information of the feature point, and the DSA image (blood vessel image) may be corrected based on the movement information of the feature point and the movement information of the pixel.

Figure 12:
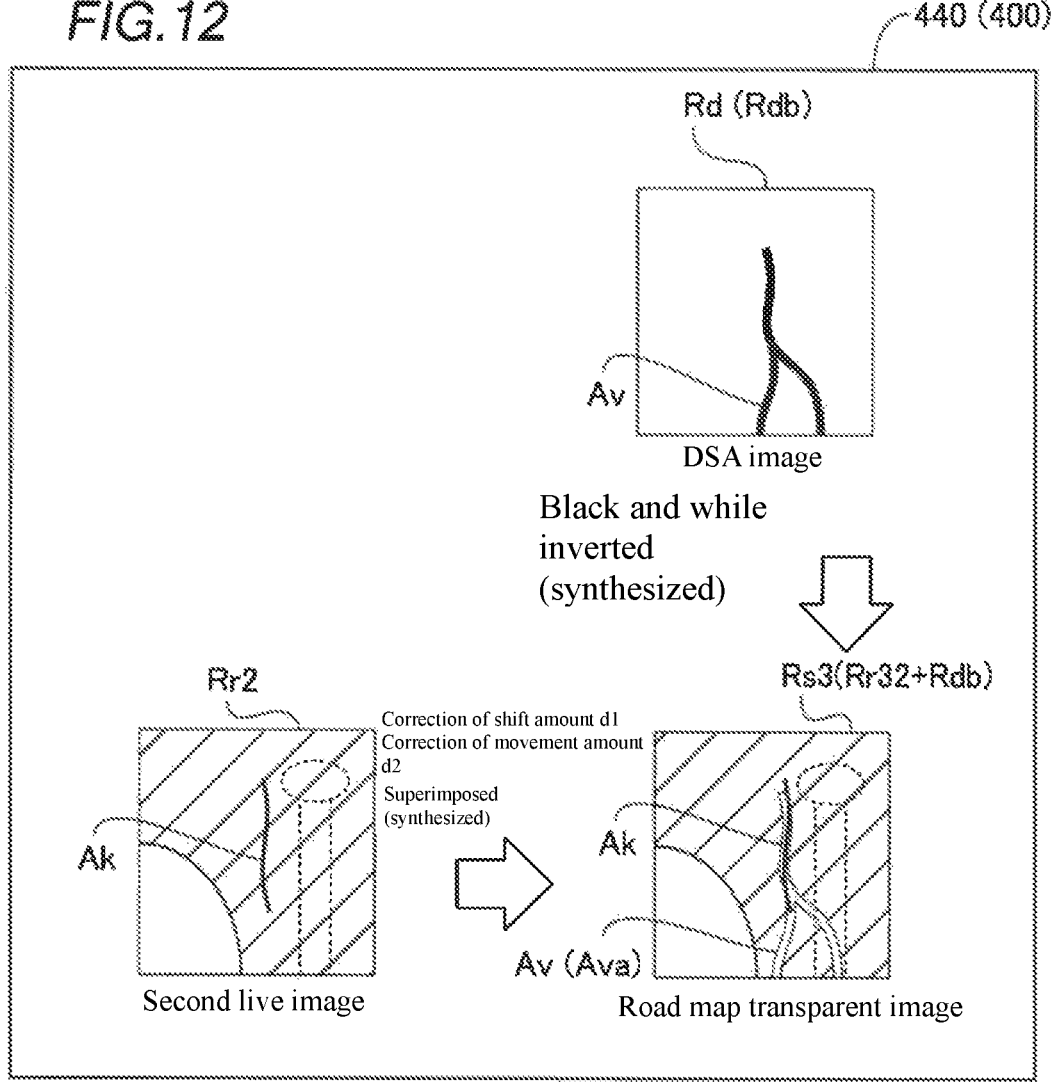
FIG. 12 is a diagram for explaining generation of the road map transparent image of the X-ray imaging apparatus according to a modified embodiment of the first to third embodiments.

Further, in the above-described embodiments, when generating the road map transparent image, an example is shown in which the image synthesis unit is configured so as to correct the DSA image (blood vessel image) and synthesize the corrected DSA image (corrected blood vessel image) with the second live image (or live image), but the present invention is not limited to this. That is, like the X-ray imaging apparatus 400 of the modification shown in FIG. 12, when generating road map transparent image Rs3, the image synthesis unit 440 may be configured to correct the second live image Rr2 based on the movement information (shift amount d1) of the feature point and the movement information (movement amount d2) of the pixel, and synthesize the corrected second live image Rr32 and DSA image Rd (corrected blood vessel image Rdb).

The invention claimed is:
1. An X-ray imaging apparatus comprising:
an imaging device including an X-ray generator that emits X-rays to a subject and an X-ray detector that detects X-rays from the X-ray generator transmitted through the subject, the imaging device captures an X-ray image of the subject; and
a processor that processes the X-ray image of the subject, the processor including,
a synthesis target image acquisition portion that acquires a synthesis target image which is a Digital Subtraction Angiography image including a contrast-enhanced blood vessel with a suppressed background structural object or without the background structural object, captured by the imaging device;
a transparent image acquisition portion that acquires a transparent image which includes the background structural object captured by the imaging device after capturing the synthesis target image;
a reference image acquisition portion that acquires a reference image which includes the background structural object appeared therein, captured by the imaging device before capturing the transparent image;
a movement information acquisition portion that extracts the background structural object from each of the reference image and the transparent image, acquires movement information of the background structural object based on the extracted background structural object, corrects the reference image based on the movement information of the background structural object, acquires a movement map representing a movement direction and a movement amount of at least some pixels belonging to the corrected reference image based on the corrected reference image and the transparent image, and acquires a smoothing movement map in which the movement map is smoothed as movement information of a pixel; and an image synthesis portion that corrects the synthesis target image or the transparent image based on the movement information of the background structural object and the movement information of the pixel, and synthesizes the corrected synthesis target image and the transparent image or synthesizes the synthesis target image and the corrected transparent image to generate the synthesized image.

2. The X-ray imaging apparatus as recited in claim 1, wherein the transparent image acquisition portion is configured to acquire the transparent image as a live image sequentially generated in real time, and wherein the image synthesis portion is configured to correct the synthesis target image or the live image based on the movement information of the background structural object and the movement information of the pixel and synthesize the corrected synthesis target image and the live image or synthesize the synthesis target image and the corrected live image to generate the synthesized image.

3. The X-ray imaging apparatus as recited in claim 2, wherein the image synthesis portion is configured to correct the synthesis target image or the live image based on the movement information of the background structural object and the movement information of the pixel each time the live image is acquired by the transparent image acquisition portion, and synthesize the corrected synthesis target image and the live image or synthesize the synthesis target image and the corrected live image to generate the synthesized image.

4. The X-ray imaging apparatus as recited in claim 2, wherein the image synthesis portion is configured to acquire a difference image between a contrast image which is the X-ray image in a state in which a contrast agent is administered to a blood vessel of a lower limb of the subject and a non-contrast image which is the X-ray image in a state in which no contrast agent is administered to the blood vessel of the subject as the synthesis target image, correct the difference image or the live image based on the movement information of the background structural object and the movement information of the pixel, and synthesize the corrected difference image and the live image or synthesize the difference image and the corrected live image to generate the synthesized image.

5. The X-ray imaging apparatus as recited in claim 4, wherein the image synthesis portion is configured to synthesize an inverted image in which at least a part of the corrected difference image is black and white inversion processed and the live image or synthesize an inverted image in which at least a part of the difference image is black and white inversion processed and the corrected live image to generate the synthesized image.

6. The X-ray imaging apparatus as recited in claim 5, wherein the image synthesis portion is configured to synthesize the inverted image and the live image including an image in which at least one of a catheter, a stent, and a guide wire inserted in the subject is projected to generate the synthesized image.

7. The X-ray imaging apparatus as recited in claim 4, wherein the reference image acquisition portion is configured to acquire the live image captured before the transparent image at an imaging position substantially the same as an imaging position of the synthesis target image as the reference image.

8. The X-ray imaging apparatus as recited in claim 4, wherein the reference image acquisition portion is configured to acquire the contrast image as the reference image.

9. The X-ray imaging apparatus as recited in claim 4, wherein the reference image acquisition portion is configured to acquire the non-contrast image as the reference image.

10. The X-ray imaging apparatus as recited in claim 1, wherein the movement information acquisition portion is configured to correct the reference image based on the movement information of the background structural object when a movement amount from the background structural object of the reference image to the background structural object of the transparent image exceeds a movement amount threshold value, and acquire movement information of the pixel based on the corrected reference image and the transparent image.

11. The X-ray imaging apparatus as recited in claim 1, wherein the movement information acquisition portion is configured to extract a plurality of the background structural objects from the reference image, extract a plurality of the background structural objects from the transparent image, correct the reference image so as to move by a mean value of the movement amount from the background structural object of the reference image to the background structural object of the transparent image, and acquire the movement information of the pixel based on the corrected reference image and the transparent image.

12. The X-ray imaging apparatus as recited in claim 1, wherein the movement information acquisition portion is configured to acquire the smoothing movement map in which high frequency components of the movement map in a spatial direction is suppressed as the movement information of the pixel.

13. The X-ray imaging apparatus as recited in claim 1, wherein the reference image is captured at the same time or at substantially the same time as the synthesis target image.

14. The X-ray imaging apparatus as recited in claim 13, wherein the reference image is captured at substantially the same time as the synthesis target image such that a body movement of the subject is not substantially occurring during the same time.

15. An X-ray image processing method comprising:
acquiring a synthesis target image which is a Digital Subtraction Angiography image including a contrast-enhanced blood vessel with a suppressed background structural object or without the background structural object;

acquiring a transparent image which includes the background structural object after capturing the synthesis target image;

acquiring a reference image which includes the background structural object before capturing the transparent image;

extracting the background structural object from each of the reference image and the transparent image;

acquiring movement information of the background structural object based on the extracted background structural object;

correcting the reference image based on the movement information of the background structural object;

acquiring a movement map representing a movement direction and a movement amount of at least some pixels belonging to the corrected reference image, based on the corrected reference image and the transparent image;

acquiring a smoothing movement map in which the movement map is smoothed as movement information of a pixel;

correcting the synthesis target image or the transparent image based on the movement information of the background structural object and movement information of the pixel; and generating a synthesized image by synthesizing the corrected synthesis target image and the transparent image or synthesizing the synthesis target image and the corrected transparent image.

* * * * *